(12) United States Patent
Tanaka et al.

(10) Patent No.: US 11,053,530 B2
(45) Date of Patent: Jul. 6, 2021

(54) BACTERIA ANALYZING METHOD AND SPECIMEN ANALYZER

(71) Applicant: Sysmex Corporation, Kobe (JP)

(72) Inventors: Masamichi Tanaka, Kobe (JP); Shota Tateyama, Kobe (JP); Masakazu Fukuda, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 317 days.

(21) Appl. No.: 14/294,643

(22) Filed: Jun. 3, 2014

(65) Prior Publication Data

US 2014/0356895 A1    Dec. 4, 2014

(30) Foreign Application Priority Data

Jun. 3, 2013  (JP) .............................. JP2013-117363
Aug. 9, 2013  (JP) .............................. JP2013-166819

(51) Int. Cl.
| | | |
|---|---|---|
| *C12Q 1/02* | (2006.01) | |
| *C12Q 1/04* | (2006.01) | |
| *G01N 15/14* | (2006.01) | |
| *G01N 15/10* | (2006.01) | |

(52) U.S. Cl.
CPC .............. *C12Q 1/02* (2013.01); *C12Q 1/04* (2013.01); *G01N 15/1459* (2013.01); *G01N 2015/1006* (2013.01); *G01N 2015/1402* (2013.01); *G01N 2015/1477* (2013.01)

(58) Field of Classification Search
CPC ....... G01N 2035/0091; G01N 15/1425; G01N 15/1459; G01N 33/493; G01N 33/5094; G01N 33/80; G01N 2333/245; G01N 2333/914; G01N 33/569; G01N 33/573; G01N 2015/1006; G01N 2015/1402; G01N 2015/1477; C12Q 1/06; C12Q 1/04; C12Q 1/18; C12Q 1/6816; C12Q 2563/173; C12Q 1/02; C12N 9/2462; C09B 23/02; Y10S 436/80; Y10T 436/143333
USPC ........ 435/39, 29, 34, 261, 32, 6.12; 436/800
IPC ............ G06F 11/30; C12Q 1/06; G01N 21/49, 33/48, 33/80
See application file for complete search history.

(56) References Cited

U.S. PATENT DOCUMENTS

| | | | | |
|---|---|---|---|---|
| 8,153,418 | B2 | 4/2012 | Kawashima | |
| 8,476,066 | B2 | 7/2013 | Takata et al. | |
| 8,647,859 | B2 | 2/2014 | Kawashima | |
| 8,669,097 | B2 | 3/2014 | Kawashima | |
| 2004/0219627 | A1* | 11/2004 | Kawashima | ............. C12Q 1/04 435/29 |
| 2010/0047856 | A1* | 2/2010 | Takata | ..................... C12Q 1/04 435/39 |
| 2011/0169837 | A1* | 7/2011 | Takata | ................... G01N 15/14 345/440.2 |
| 2013/0052645 | A1* | 2/2013 | Scott | ........................ C12Q 1/04 435/6.11 |

FOREIGN PATENT DOCUMENTS

| | | |
|---|---|---|
| CN | 101625324 A | 1/2010 |
| CN | 102559912 A | 7/2012 |
| EP | 2 348 301 A1 | 7/2011 |
| JP | H05-322885 A | 12/1993 |
| JP | H09-119926 A | 5/1997 |
| JP | 2004-305173 A | 11/2004 |
| JP | 2010-019557 | 1/2010 |
| JP | 2010-019557 A | 1/2010 |

OTHER PUBLICATIONS

PubMed Health. 2013. Understanding Urine Tests. National Library of Medicine. Jan. 22, 2013).*

* cited by examiner

*Primary Examiner* — Robert J Yamasaki
(74) *Attorney, Agent, or Firm* — Brinks Gilson & Lione

(57) ABSTRACT

Disclosed is a bacteria analyzing method comprising: irradiating with light a measurement sample prepared by mixing a specimen and a reagent; obtaining two types of optical information from each of at least some particles contained in the measurement sample; and generating a measurement result of the specimen with a flag representing morphological characteristics of bacteria contained in the specimen based on both of: (i) information indicative of a characteristic of a distribution pattern of particles plotted in a first region of a coordinate space including at least two axes, wherein the two types of optical information are scalable along the respective axes, and (ii) information representing a number of particles plotted in a second region being a part of the first region.

14 Claims, 27 Drawing Sheets

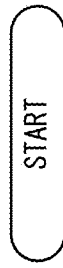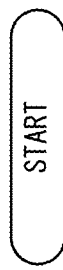

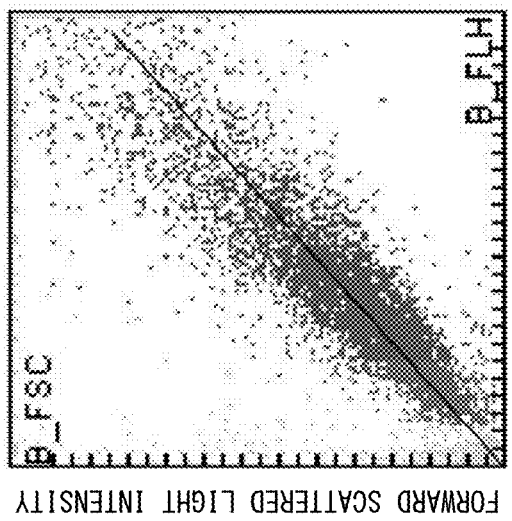 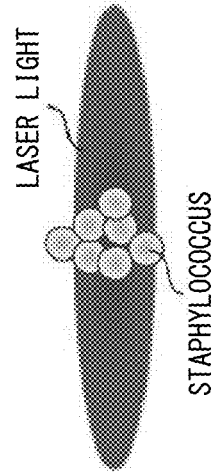
FIG. 7A
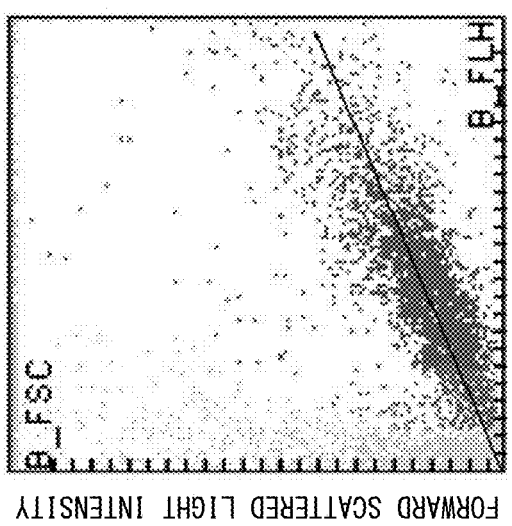 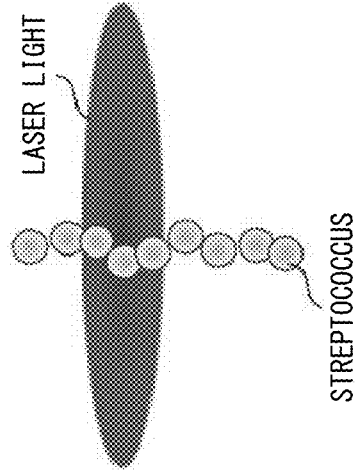
FIG. 7B
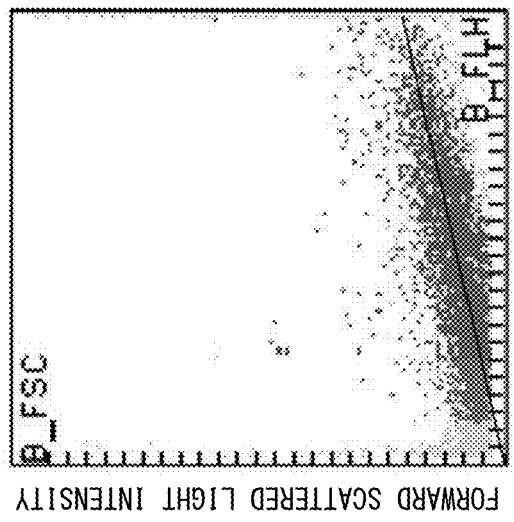 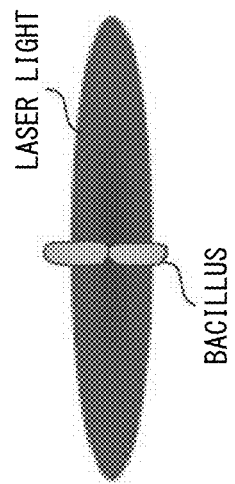
FIG. 7C FIG. 8A
<SCATTERGRAM DATA TABLE Ts>
| X\Y | 1 | 2 | ... | n |
|---|---|---|---|---|
| 1 | G11 | G21 | ... | Gn1 |
| 2 | G12 | G22 | ... | Gn2 |
| ... | ... | ... | ... | ... |
| n | G1n | G2n | ... | Gnn |
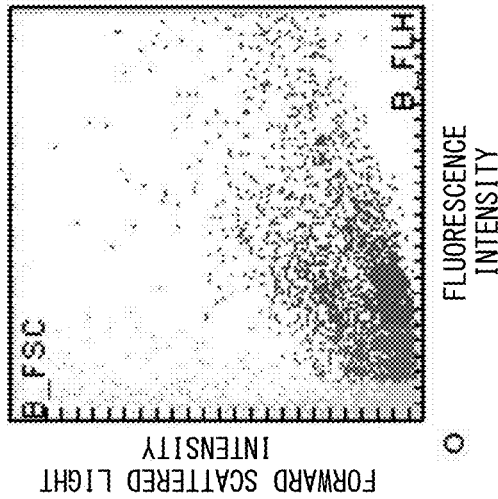
FIG. 8B
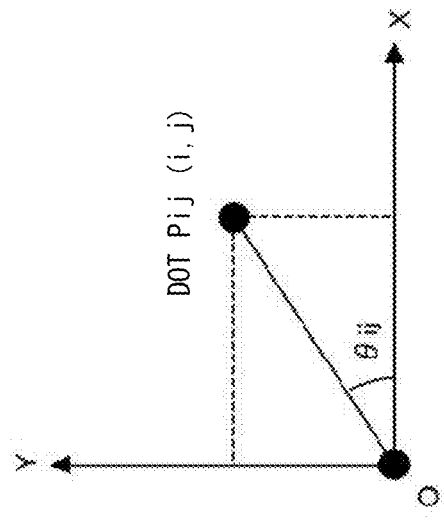
FIG. 8C <DECLINATION DATA TABLE Td>

| X\Y | 1 | 2 | ... | n |
|---|---|---|---|---|
| 1 | θ11 | θ21 | ... | θn1 |
| 2 | θ12 | θ22 | ... | θn2 |
| ... | ... | ... | ... | ... |
| n | θ1n | θ2n | ... | θnn |

<HISTOGRAM DATA TABLE Th>

| k | (θk) | Fk |
|---|---|---|
| 1 | (θ1) | F1 |
| 2 | (θ2) | F2 |
| ... | ... | ... |
| m | (θm) | Fm |

FIG. 15A

CONCORDANCE RATE 70.6% (60/85)

|  | BACILLUS | COCCUS | MIX |
|---|---|---|---|
| SENSITIVITY | 78.1% (50/64) | 45.5% (5/11) | 50.0% (5/10) |
| PPV | 90.9% (50/55) | 62.5% (5/8) | 22.7% (5/22) |

| EMBODIMENT | | | GRAM STAIN | | | |
|---|---|---|---|---|---|---|
| | | | BACILLUS | COCCUS | MIX | |
| | BACILLUS | | 50 | 0 | 5 | 55 |
| | COCCUS | | 3 | 5 | 0 | 8 |
| | MIX | | 11 | 6 | 5 | 22 |
| | | | 64 | 11 | 10 | 85 |

FIG. 15B

CONCORDANCE RATE 63.5% (54/85)

|  | BACILLUS | COCCUS | MIX |
|---|---|---|---|
| SENSITIVITY | 75.0% (48/64) | 54.5% (6/11) | 0.0% (0/10) |
| PPV | 85.7% (48/56) | 40.0% (6/15) | 0.0% (0/14) |

| PRIOR ART | | | GRAM STAIN | | | |
|---|---|---|---|---|---|---|
| | | | BACILLUS | COCCUS | MIX | |
| | BACILLUS | | 48 | 3 | 5 | 56 |
| | COCCUS | | 4 | 6 | 5 | 15 |
| | MIX | | 12 | 2 | 0 | 14 |
| | | | 64 | 11 | 10 | 85 |

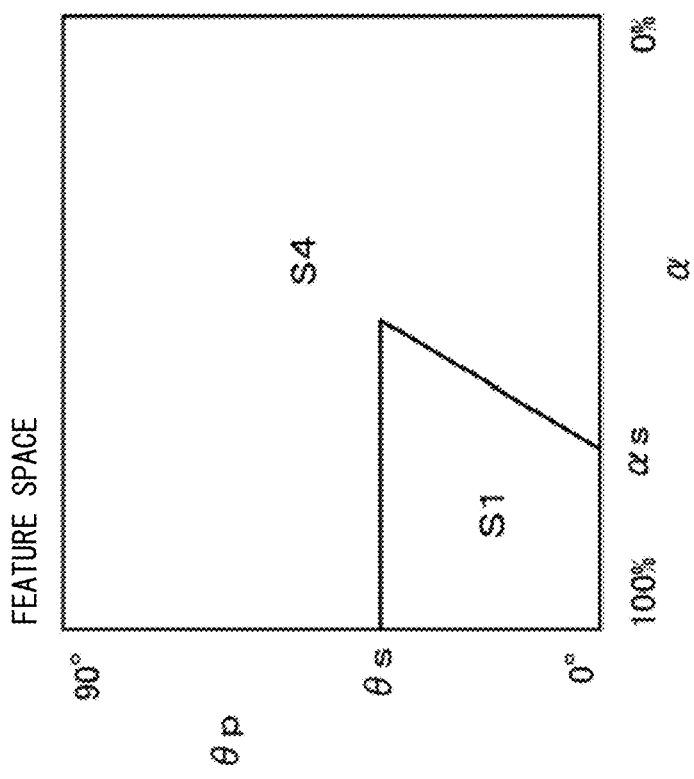

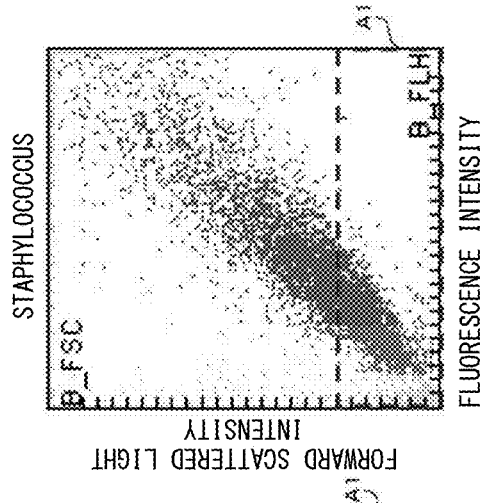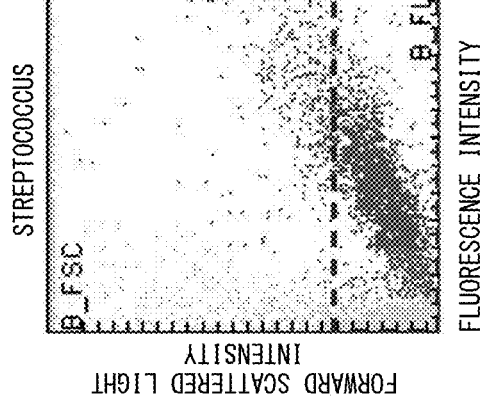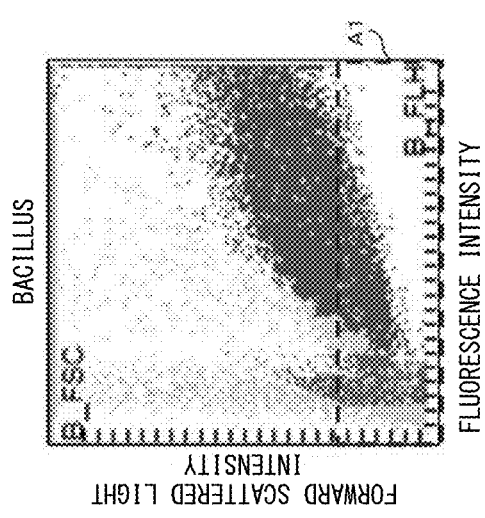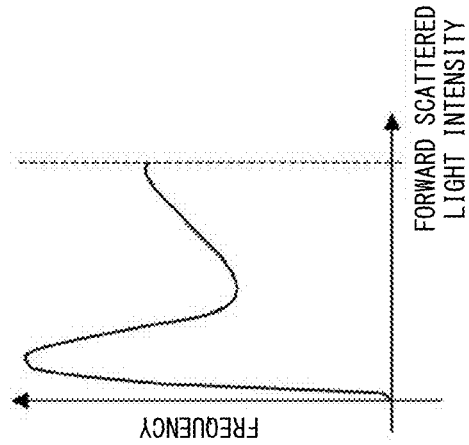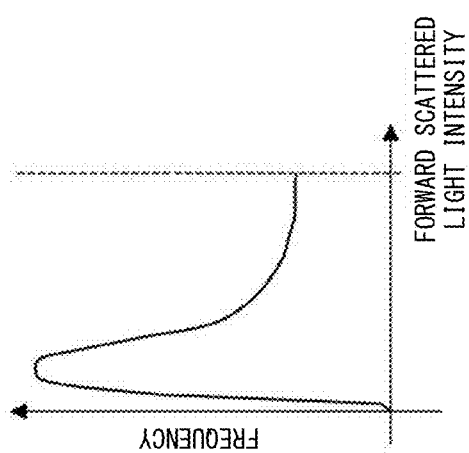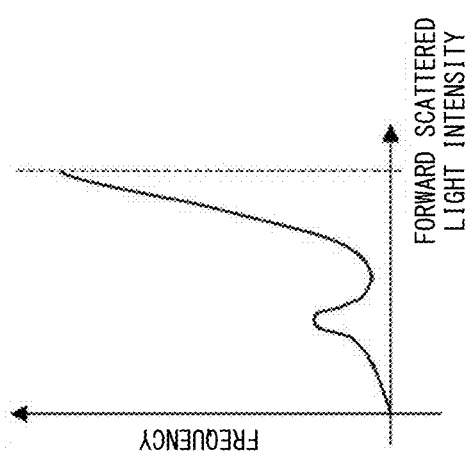

FIG. 23A

CONCORDANCE RATE 77.6% (66/85)

|  | BACILLUS | COCCUS/MIX |
|---|---|---|
| SENSITIVITY | 78.1% (50/64) | 76.2% (16/21) |
| PPV | 90.9% (50/55) | 53.3% (16/30) |

|  |  | GRAM STAIN | | | |
|---|---|---|---|---|---|
|  |  | BACILLUS | COCCUS | MIX | |
| EMBODIMENT | BACILLUS | 50 | 0 | 5 | 55 |
|  | COCCUS/MIX | 14 | 11 | 5 | 30 |
|  |  | 64 | 11 | 10 | 85 |

FIG. 23B

CONCORDANCE RATE 83.5% (71/85)

|  | BACILLUS | COCCUS/MIX |
|---|---|---|
| SENSITIVITY | 89.1% (57/64) | 66.7% (14/21) |
| PPV | 89.1% (57/64) | 66.7% (14/21) |

|  |  | GRAM STAIN | | | |
|---|---|---|---|---|---|
|  |  | BACILLUS | COCCUS | MIX | |
| MODIFICATION | BACILLUS | 57 | 2 | 5 | 64 |
|  | COCCUS/MIX | 7 | 9 | 5 | 21 |
|  |  | 64 | 11 | 10 | 85 |

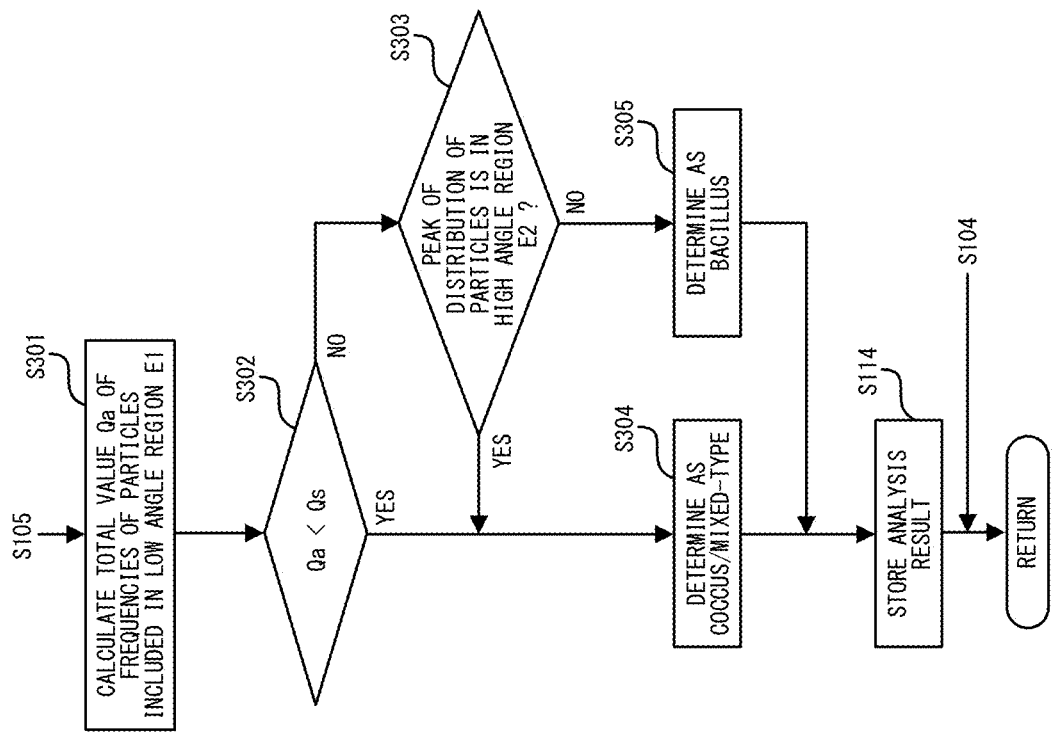
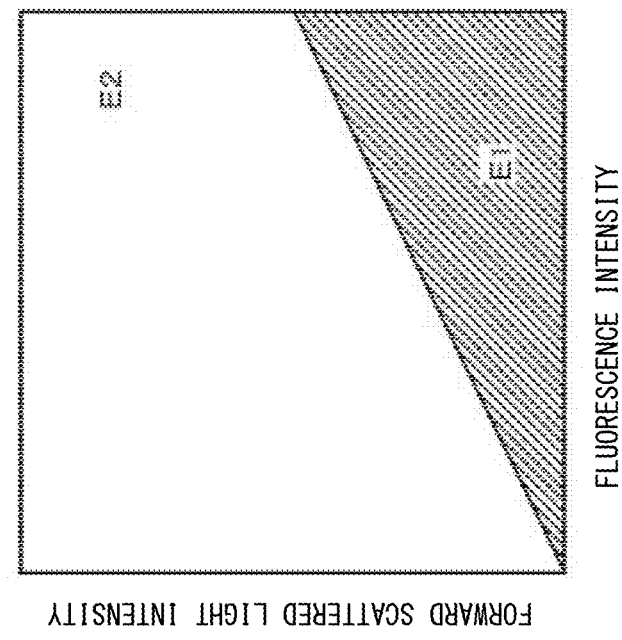

BACTERIA ANALYZING METHOD AND SPECIMEN ANALYZER

RELATED APPLICATIONS

This application claims priority under 35 U.S.C. § 119 to Japanese Patent Application Nos. 2013-117363 filed on Jun. 3, 2013 and 2013-166819 filed on Aug. 9, 2013, the entire content of which are hereby incorporated by reference.

FIELD OF THE INVENTION

The present invention relates to a bacteria analyzing method in which a measurement sample prepared from a specimen and a reagent is irradiated with light to obtain optical information, and based on the optical information, bacteria contained in the specimen is analyzed. The present invention also relates to a specimen analyzer provided with a function of analyzing bacteria.

BACKGROUND OF THE INVENTION

At present, in laboratory tests and the like, bacteria analyzers which detect bacteria in urine and bacteria contained in a cultured specimen are used. In recent years, bacteria analyzers provided with a function of not only detecting bacteria contained in a specimen but also determining the types of bacteria have been proposed.

U.S. Patent application publication No. 2010-0047856 discloses a method for determining the form of bacteria by use of a scattergram. In this method, a scattergram which uses, as parameters, scattered light information and fluorescence information of bacteria contained in a specimen is generated. Then, the angle of each bacterium relative to the origin of the scattergram is detected. A histogram of the angle and the number of particles is generated. Based on the angle where a peak emerges on the histogram, the form of the bacteria is determined. In this method, if there is one peak in the histogram, it is determined that form of bacteria is one, and the type of the bacteria is determined. If there are a plurality of peaks in the histogram, it is determined that a plurality of form of bacteria are contained, and the types of bacteria are determined.

The present invention has been made to improve an accuracy of determination of morphologic type of bacteria contained in a specimen.

SUMMARY OF THE INVENTION

A first aspect of the present invention is a bacteria analyzing method comprising: irradiating with light a measurement sample prepared by mixing a specimen and a reagent; obtaining two types of optical information from each of at least some particles contained in the measurement sample; and generating a measurement result of the specimen with a flag representing morphological characteristics of bacteria contained in the specimen based on both of:
(i) information indicative of a characteristic of a distribution pattern of particles plotted in a first region of a coordinate space including at least two axes, wherein the two types of optical information are scalable along the respective axes, and
(ii) information representing a number of particles plotted in a second region being a part of the first region.

A second aspect of the present invention is a bacteria analyzing method comprising: forming a beam spot in a flow cell by emitting light from a light source; flowing, in the flow cell, a measurement sample prepared by mixing a specimen and a reagent; obtaining a first parameter of scattered light intensity and a second parameter of fluorescence intensity generated from each of at least some of particles in the measurement sample that has passed through the beam spot; plotting the at least some of particles in the measurement sample onto a coordinate space according to the first and second parameters, wherein the coordinate space including at least two axes along which the first and second parameters are scalable; and generating a measurement result of the specimen with a flag regarding morphological characteristics of bacteria based on both of (i) a representative value of relationship of the first and second parameters of at least some of particles plotted in the coordinate space; and (ii) a ratio of a first number of particles plotted in a first region of the coordinate space and a second number of particles plotted in a second region being a part of the first region.

A third aspect of the present invention is a specimen analyzer comprising: a light source unit configured to irradiate with light a measurement sample prepared by mixing a specimen and a reagent; an optical information obtaining unit configured to obtain two types of optical information for each of at least some particles contained in the measurement sample by detecting light generated from the measurement sample due to light from the light source unit; and a processing unit configured to process the obtained two types of optical information, wherein the processing unit is programmed to generate a measurement result of the specimen with a flag representing morphological characteristics of bacteria based on both of (i) information indicative of a characteristic of a distribution pattern of particles plotted in a first region of a coordinate space including at least two axes, wherein the two types of optical information are scalable along the respective axes, and (ii) information representing a number of particles plotted in a second region being a part of the first region.

A fourth aspect of the present invention is a bacteria analyzing method comprising: flowing a measurement sample in a flow cell; irradiating with light the measurement sample flowing in the flow cell; obtaining at least first optical information and second optical information from each of at least some particles contained in the measurement sample, wherein the first optical information and the second optical information are respectively scalable along two axes of a coordinate space; obtaining first characteristic information and second characteristic information from the coordinate space, wherein the first characteristic information represents a position on the coordinate space where particles are concentrated, and the second characteristic information represents a relation between an entire distribution of particles and a partial distribution particles on the coordinate space; and determining, based on the first and second characteristic information, a morphologic type of bacteria contained in the measurement sample.

BRIEF DESCRIPTION OF THE DRAWINGS

FIGS. 6A and 6B show flow charts of a measurement process performed on a specimen and an analysis process according to the embodiment;

FIGS. 7A-7C illustrate scattergrams in accordance with the morphologic types of bacteria according to the embodiment;

FIGS. 8A-8C show scattergrams according to the embodiment;

FIGS. 15A and 15B show verification examples of determination results of the morphologic type of bacteria according to the embodiment;

FIGS. 18A and 18B are schematic diagrams showing a feature space for determining the morphologic type of bacteria according to a modification and a verification example of determination results of the morphologic type of bacteria;

FIGS. 19A-19F illustrate scattergrams of forward scattered light intensity and fluorescence intensity and histograms thereof in accordance with the morphologic type of bacteria according to a modification;

FIGS. 23A and 23B show verification examples of determination results of the morphologic types of bacteria according to the modification;

FIGS. 27A and 27B illustrate angle regions set on a scattergram of forward scattered light intensity and fluorescence intensity and a flow chart showing an analysis process according to a modification.

DETAILED DESCRIPTION OF THE PREFERRED EMBODIMENTS

Figure 1:
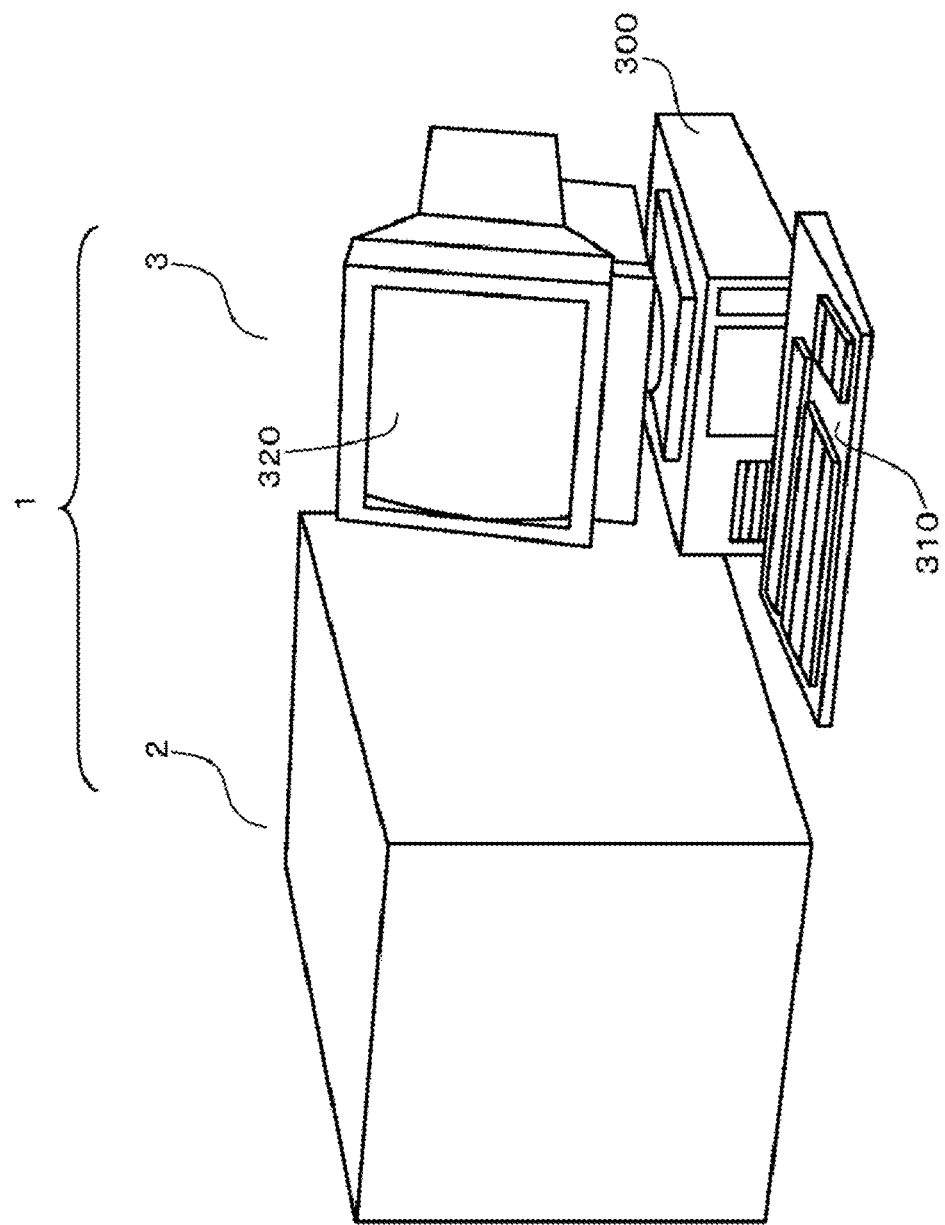
FIG. 1 shows the configuration of a urine specimen analyzer according to an embodiment.

FIG. 1 shows the configuration of a urine specimen analyzer 1 according to the present embodiment.

The urine specimen analyzer 1 includes a measurement apparatus 2 and an information processing apparatus 3. The measurement apparatus 2 optically measures bacteria and urine formed elements such as white blood cells contained in a urine specimen, by use of a flow cytometer. The information processing apparatus 3 analyzes a measurement result from the measurement apparatus 2 to obtain an analysis result. The information processing apparatus 3 causes a display unit 320 to display the analysis result.

Figure 2:
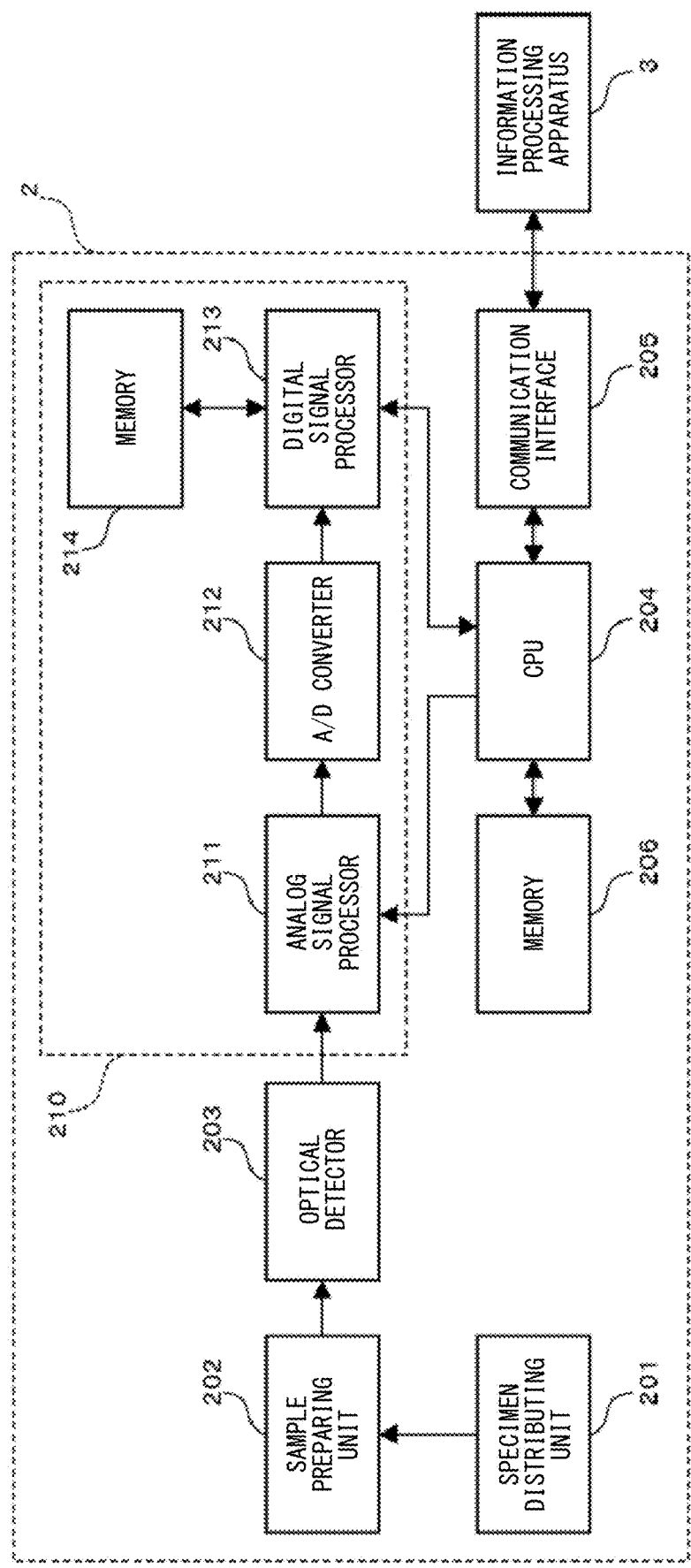
FIG. 2 shows the configuration of a measurement apparatus according to the embodiment.

As shown in FIG. 2, the measurement apparatus 2 includes a specimen distributing unit 201, a sample preparing unit 202, an optical detector 203, a signal processor 210, a CPU 204, a communication interface 205, and a memory 206. The signal processor 210 includes an analog signal processor 211, an A/D converter 212, a digital signal processor 213, and a memory 214.

The specimen distributing unit 201 includes an aspiration tube 201*a* (see FIG. 3), and a pump (not shown). By driving the pump, the specimen distributing unit 201 aspirates a urine specimen in a specimen container into the aspiration tube 201*a*, and dispenses the aspirated urine specimen into a mixing chamber in the sample preparing unit 202.

The sample preparing unit 202 includes reagent containers, mixing chambers, and a pump (not shown). The sample preparing unit 202 supplies a diluent and a stain solution from the reagent containers into the mixing chamber. Accordingly, in the mixing chamber, the specimen supplied from the specimen distributing unit 201 and the diluent and the stain solution are mixed, whereby a measurement sample is prepared. The measurement sample prepared in the mixing chamber is supplied, by the pump, to a flow cell 203*c* (see FIG. 4) of the optical detector 203 along with a sheath liquid.

The optical detector 203 irradiates the measurement sample flowing in the flow cell 203*c* with laser light. At the same time, the optical detector 203 receives forward scattered light, fluorescence, and side scattered light generated at the flow cell 203*c*, with three light receiving units, respectively. Each light receiving unit continuously outputs an analog signal corresponding to the intensity of the received light, to the analog signal processor 211. The intensity of the received light in each light receiving unit changes in a pulse form every time a particle passes through the flow cell 203*c*. The analog signal processor 211 amplifies each analog signal outputted from the optical detector 203, and outputs each amplified analog signal to the A/D converter 212.

The A/D converter 212 converts the respective analog signals derived from the forward scattered light, the fluorescence, and the side scattered light and amplified by the analog signal processor 211, into digital signals, and outputs the digital signals to the digital signal processor 213. Based on the digital signal of the forward scattered light outputted from the A/D converter 212, the digital signal processor 213 detects particles that have passed through the flow cell 203*c*, and obtains data indicative of characteristics of the forward scattered light, the fluorescence, and the side scattered light with respect to each detected particle. Specifically, when a digital value of forward scattered light exceeds a threshold value, the digital signal processor 213 detects a particle. The digital signal processor 213 extracts data indicative of a characteristic of a portion, of a pulse of forward scattered light, that has exceeded the threshold value. Similarly, the digital signal processor 213 extracts data indicative of characteristics of a pulse of fluorescence and a pulse of side scattered light at the time corresponding to the pulse of the forward scattered light. The extracted data of each particle is stored in the memory 214.

The CPU 204 obtains, from the data stored in the memory 214, the levels of pulse signals of forward scattered light and fluorescence for each particle. The level of a pulse signal of forward scattered light indicates the intensity of forward scattered light generated by one particle having passed through the flow cell 203c. The larger the surface area of a bacterium when irradiated with laser light is, the more the amount of laser light scattered by the bacterium is, and thus, the level of the pulse signal of forward scattered light is increased. That is, the level of a pulse signal of forward scattered light reflects the surface area of the bacterium. The level of a pulse signal of fluorescence indicates the intensity of fluorescence generated by one particle having passed through the flow cell 203c. The level of a pulse signal of fluorescence reflects the degree of staining of the particle, and in the case of a bacterium, in particular, reflects the degree of staining of nucleic acid of the bacterium.

After obtaining the levels of the pulse signals of forward scattered light and fluorescence, the CPU 204 generates a data group (hereinafter, referred to as "measurement data") of a forward scattered light intensity and a fluorescence intensity of each bacterium that has passed through the flow cell 203c, based on the levels of the pulse signals. The CPU 204 outputs the measurement data to the information processing apparatus 3 via the communication interface 205. The CPU 204 receives control signals from the information processing apparatus 3 via the communication interface 205, and drives the units of the measurement apparatus 2 in accordance with the control signals.

The communication interface 205 transmits, to the information processing apparatus 3, the measurement data outputted from the CPU 204, and receives control signals outputted from the information processing apparatus 3. The memory 206 is used as a work area for the CPU 204.

Figure 3:
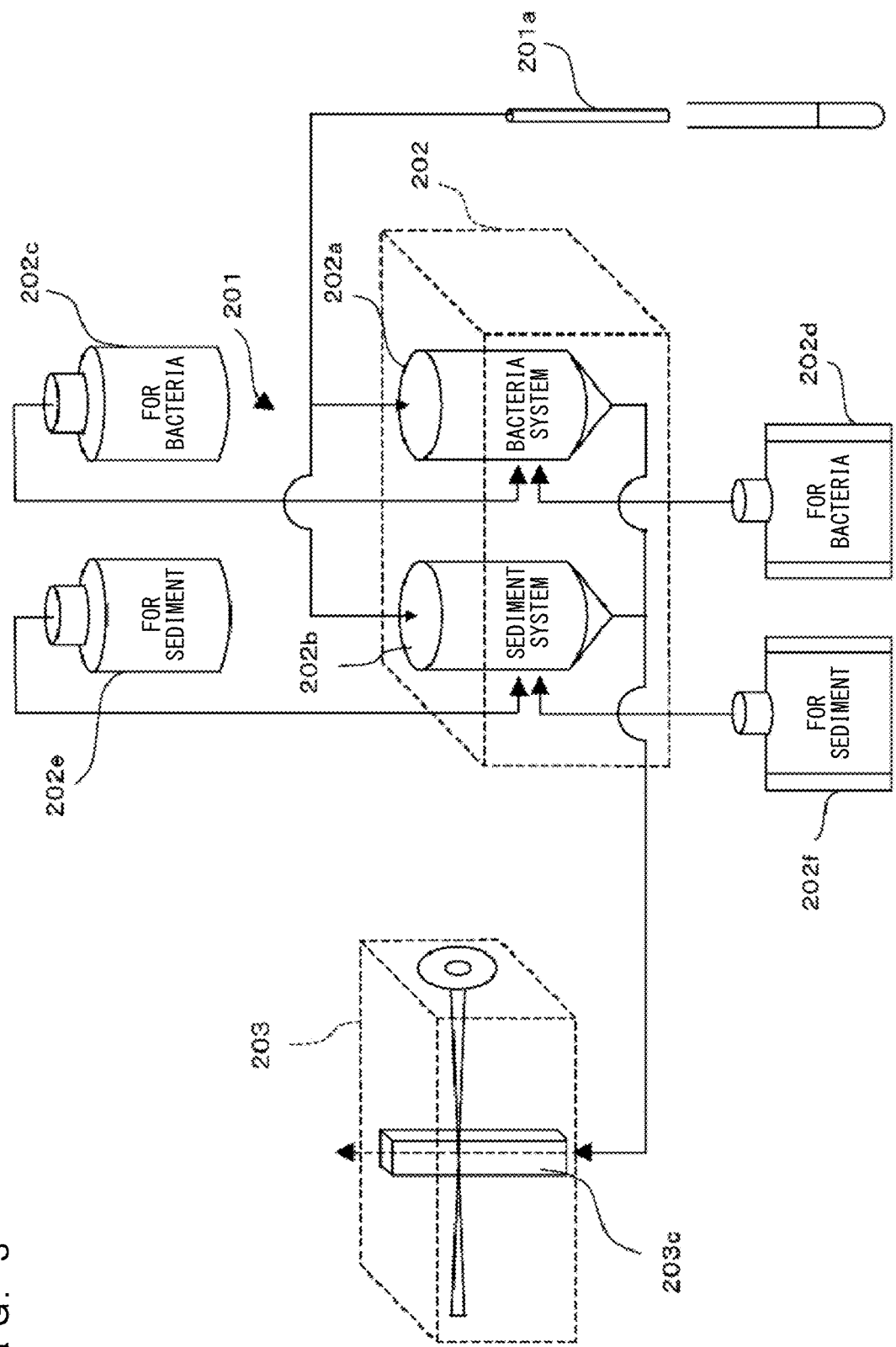
FIG. 3 shows the configurations of a sample preparing unit and an optical detector according to the embodiment.

FIG. 3 is a schematic diagram illustrating a functional configuration of the sample preparing unit 202 and the optical detector 203. The specimen distributing unit 201 aspirates a urine specimen in a test tube via the aspiration tube 201a. The sample preparing unit 202 includes a mixing chamber 202a and a mixing chamber 202b. The specimen distributing unit 201 distributes aliquots of the urine specimen into each of the mixing chamber 202a and the mixing chamber 202b.

The aliquot in the mixing chamber 202a is mixed with a diluent 202c and a stain solution 202d, whereby a measurement sample in which particles are stained by the dye contained in the stain solution 202d is prepared. This measurement sample is used for analyzing bacteria in the urine specimen.

The aliquot in the mixing chamber 202b is mixed with a diluent 202e and a stain solution 202f, whereby a measurement sample in which particles are stained by the dye contained in the stain solution 202f is prepared. This measurement sample is used for analyzing urine formed elements that are relatively large, such as red blood cells, white blood cells, epithelial cells, and casts.

The measurement sample in the mixing chamber 202b is sent to the optical detector 203, first, and then, the measurement sample in the mixing chamber 202a is sent to the optical detector 203. The measurement sample sent to the optical detector 203 forms a thin sample flow surrounded with the sheath liquid in the flow cell 203c. The optical detector 203 irradiates the sample flow with laser light. This operation is automatically performed by a drive unit, an electromagnetic valve, and the like not shown operating under control of the information processing apparatus 3.

Figure 4:
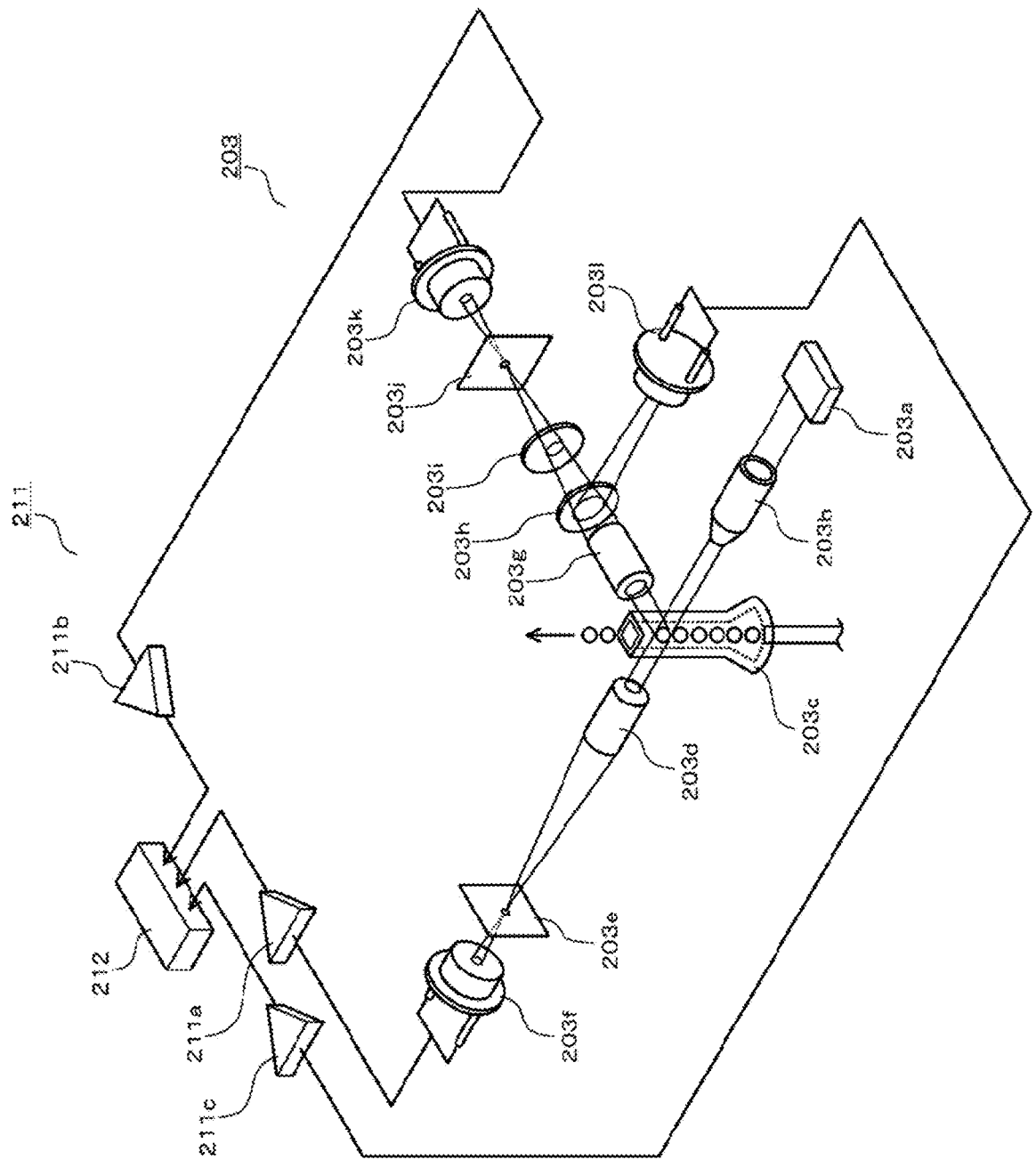
FIG. 4 is a schematic diagram showing the configurations of the optical detector and an analog signal circuit according to the embodiment.

FIG. 4 is a schematic diagram showing the configuration of the optical detector 203 and the analog signal processor 211 in the measurement apparatus 2.

The optical detector 203 includes a light source 203a, an irradiation lens unit 203b, the flow cell 203c, a condenser lens 203d, a pin hole plate 203e, a light receiving unit 203f, a condenser lens 203g, a dichroic mirror 203h, an optical filter 203i, a pin hole plate 203j, a light receiving unit 203k, and a light receiving unit 203l. The analog signal processor 211 includes amplifiers 211a, 211b, and 211c. The light receiving unit 203f is a photodiode. Each of the light receiving unit 203k and the light receiving unit 203l is a photomultiplier. It should be noted that the photoelectric conversion elements to be used as light receiving units may be modified as appropriate.

Laser light emitted from the light source 203a forms, by means of the irradiation lens unit 203b, a flat beam spot inside the flow cell 203c and in a direction perpendicular to the sample flow.

The condenser lens 203d is arranged in the advancing direction of laser light emitted from the light source 203a. Forward scattered light generated at the flow cell 203c is converged by the condenser lens 203d, and passes through the pin hole plate 203e to be received by the light receiving unit 203f.

The condenser lens 203g is arranged in a direction that crosses the advancing direction of laser light emitted from the light source 203a. Fluorescence and side scattered light generated at the flow cell 203c are converged by the condenser lens 203g and enters the dichroic mirror 203h. The dichroic mirror 203h separates fluorescence and side scattered light from each other. Fluorescence separated by the dichroic mirror 203h passes through the optical filter 203i and the pin hole plate 203j to be received by the light receiving unit 203k. Side scattered light separated by the dichroic mirror 203h is received by the light receiving unit 203l.

The light receiving unit 203f, the light receiving unit 203k, and the light receiving unit 203l output electric signals in accordance with the intensities of the received forward scattered light, fluorescence, and side scattered light, respectively. The amplifiers 211a, 211b, and 211c amplify electric signals outputted from the PD 203f, the PMT 203k, and the PMT 203l, respectively, and output the amplified electric signals to the A/D converter 212. The amplifiers 211a, 211b, and 211c form the analog signal processor 211 shown in FIG. 2.

Figure 5:
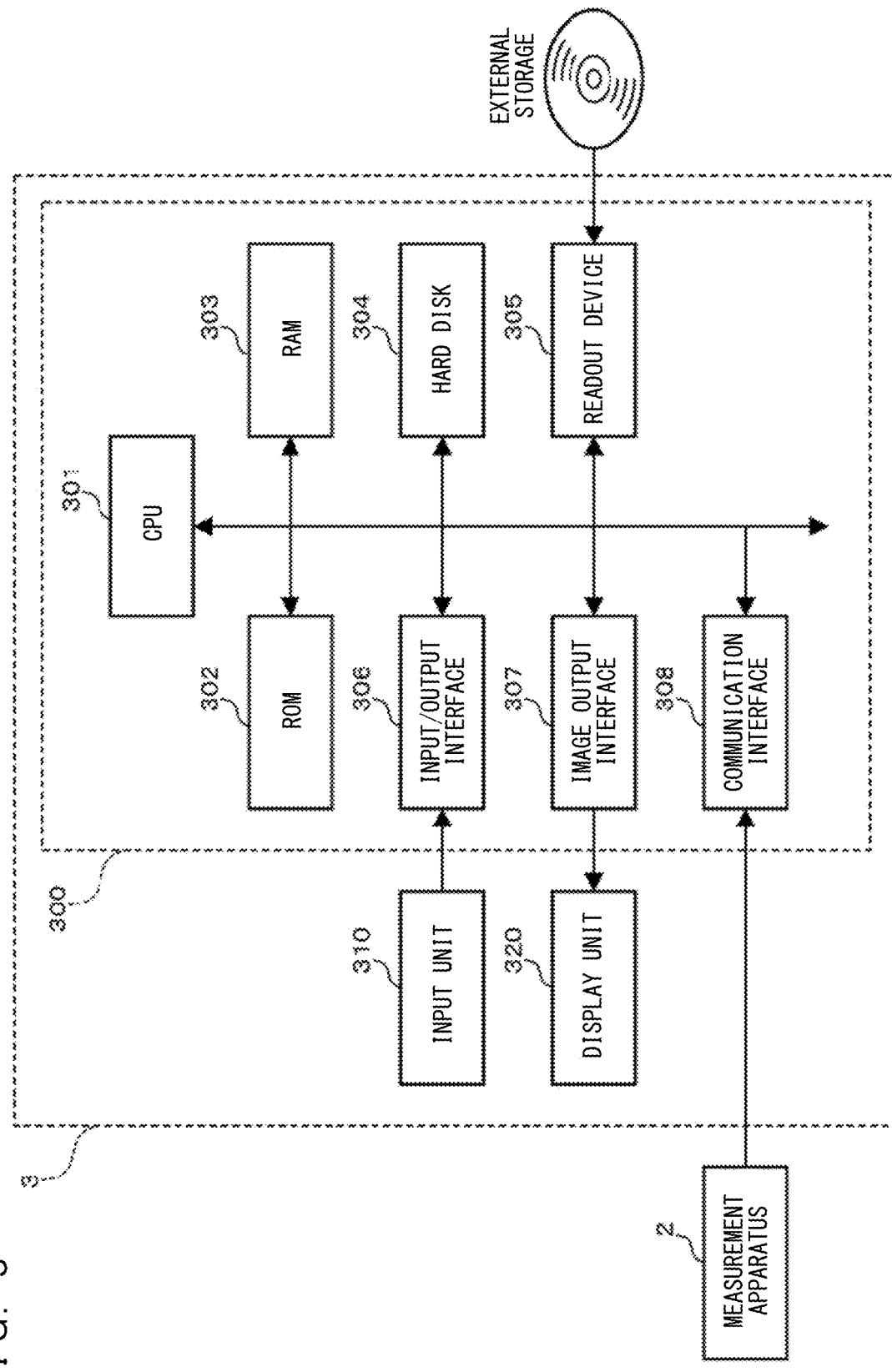
FIG. 5 shows the configuration of an information processing apparatus according to the embodiment.

FIG. 5 shows the configuration of the information processing apparatus 3.

The information processing apparatus 3 includes a personal computer. The information processing apparatus 3 is composed of a body 300, an input unit 310, and the display unit 320 (see FIG. 1). The body 300 includes a CPU 301, a ROM 302, a RAM 303, a hard disk 304, a readout device 305, an input/output interface 306, an image output interface 307, and a communication interface 308.

The CPU 301 executes computer programs stored in the ROM 302 and computer programs loaded onto the RAM 303. The RAM 303 is used for reading out computer programs stored in the ROM 302 and the hard disk 304. The RAM 303 is also used as a work area for the CPU 301 when the CPU 301 executes these computer programs.

In the hard disk 304, various computer programs, such as an operating system and application programs, to be executed by the CPU 301 and data to be used in execution of the computer programs are installed. Moreover, in the hard disk 304, measurement data received from the measurement apparatus 2 is stored.

Moreover, in the hard disk 304, a program for obtaining the number of bacteria and other urine formed elements contained in a specimen based on the measurement data and for performing analysis of the specimen, and a display program for displaying an analysis result on the display unit 320 are installed. Since these programs are installed, an analysis process and a display process described later are performed. That is, the CPU 301 is provided, by virtue of these programs, with a function of performing processes in FIG. 6B and FIG. 13 described later, and a function of displaying a screen shown in FIG. 14.

The readout device 305 is implemented by a CD drive, a DVD drive, or the like, and can read out computer programs and data stored in an external storage such as a storage medium. Accordingly, programs to be executed in the information processing apparatus 3 can be updated via an external storage such as a storage medium.

To the input/output interface 306, the input unit 310 composed of a mouse and a key board is connected. By a user using the input unit 310, an instruction to the information processing apparatus 3 is given. The image output interface 307 is connected to the display unit 320 implemented by a display or the like, and outputs a video signal corresponding to image data to the display unit 320. The display unit 320 displays an image based on the video signal inputted by the image output interface 307.

The communication interface 308 allows reception of measurement data transmitted from the measurement apparatus 2. The measurement data is stored in the hard disk 304.

FIGS. 6A and 6B show flow charts of control performed by the CPU 204 of the measurement apparatus 2 and control performed by the CPU 301 of the information processing apparatus 3. FIG. 6A is a flow chart showing a measurement process performed by the CPU 204 of the measurement apparatus 2. FIG. 6B is a flow chart showing an analysis process performed by the CPU 301 of the information processing apparatus 3.

With reference to FIG. 6B, upon receiving a measurement start instruction from a user via the input unit 310 (S11: YES), the CPU 301 transmits a measurement start signal to the measurement apparatus 2 (S12). Subsequently, the CPU 301 determines whether measurement data has been received (S13). When measurement data has not been received (S13: NO), the process is caused to wait.

On the other hand, with reference to FIG. 6A, upon receiving the measurement start signal from the information processing apparatus 3 (S21: YES), the CPU 204 performs measurement of a specimen described above (S22). Upon completion of the measurement of the specimen, the CPU 204 transmits measurement data to the information processing apparatus 3 (S23), and the process is returned to S21.

With reference to FIG. 6B, upon receiving the measurement data from the measurement apparatus 2 (S13: YES), the CPU 301 stores the measurement data in the hard disk 304 and performs an analysis process based on the measurement data (S14). Subsequently, the CPU 301 causes the display unit 320 to display an analysis result obtained in S14 (S15). Then, the process is returned to S11.

Next, the "analysis process" of S14 shown in FIGS. 6A and 6B will be described.

With reference to FIGS. 7A to 7C, the theory of determining the morphologic type of bacteria will be described.

FIG. 7A illustrates a two-dimensional scattergram when bacilli are mainly contained in a measurement sample. FIG. 7B illustrates a two-dimensional scattergram when *Streptococci* are mainly contained in a measurement sample. FIG. 7C illustrates a two-dimensional scattergram when *Staphylococci* are mainly contained in a measurement sample. In lower parts of FIG. 7A to FIG. 7C, irradiation states of laser light (see FIG. 4) to the respective morphologic types of bacteria are schematically shown. As described with reference to FIG. 4, laser light forms a flat beam spot in the flow cell 203c, and a sample flow containing bacteria passes through the beam spot from therebelow. For reference, each of FIGS. 7A to 7C is provided with a straight line indicating an angle along which a largest dots are plotted.

In measurement of bacteria, the larger the size (surface area) of a bacterium, the higher the forward scattered light intensity (the peak value) is, and the higher the degree of staining of a bacterium, the higher the fluorescence intensity is. It means that the distribution state of dots on a two-dimensional scattergram differs depending on the morphologic type of bacteria.

As shown in the lower part of FIG. 7A, in the case of *Bacillus*, each bacterium has an elongated rod or cylindrical shape, and thus, compared with *Streptococcus* and *Staphylococcus*, the surface area of the bacteria irradiated with laser light is small. In the example shown in FIG. 7A, a part of two consecutive bacilli is irradiated with laser light. Other than the state shown in FIG. 7A, there may be a case where only one *Bacillus* is irradiated with laser light. Thus, in the case of *Bacillus*, since the surface area of bacteria irradiated with laser light is small, the forward scattered light intensity is low. Therefore, when bacilli are mainly contained in a measurement sample, a two-dimensional scattergram in which most dots are distributed in a lower region is obtained, as shown in FIG. 7A.

As shown in the lower part of FIG. 7B, in the case of *Streptococcus*, each bacterium has a substantially round shape, and the bacteria are linearly connected to each other. Thus, the surface area of *Streptococci* irradiated with laser light is larger than that of bacilli. Therefore, when *Streptococci* are mainly contained in a measurement sample, the forward scattered light intensity thereof tends to be greater than that of bacilli, and thus, a two-dimensional scattergram in which dots are distributed upper than in the case of bacilli is obtained, as shown in FIG. 7B.

As shown in the lower part of FIG. 7C, in the case of *Staphylococcus*, as in the case of *Streptococcus*, each bacterium has a substantially round shape, but the degree of aggregation of bacteria is higher than in the case of *Streptococcus*. Therefore, the surface area of *Streptococci* irradiated with laser light is larger than that of *Streptococci*. Therefore, when *Streptococci* are mainly contained in a measurement sample, the forward scattered light intensity tends to be further higher than that of *Streptococci*, and thus, a two-dimensional scattergram in which dots are distributed further upper than in the case of *Streptococci* is obtained, as shown in FIG. 7C.

With reference to FIGS. 7A to 7C, the declinations (deflection angles) from the horizontal axis to the respective straight lines are different for the respective morphologic types of bacteria. Therefore, a declination is determined from a two-dimensional scattergram having a horizontal axis representing fluorescence intensity and a vertical axis representing forward scattered light intensity, and the magnitude of the determined declination is compared with a predetermined threshold value, whereby whether the bacteria contained in the measurement sample are *Bacillus* or *coccus* (*Streptococcus, Staphylococcus*) can be determined. In the present embodiment, based on this theory, the morphologic type of bacteria contained in a measurement sample is determined.

In a case where a plurality of morphologic types of bacteria, i.e., *Bacillus* and *coccus* are contained in a measurement sample, dot distribution in a two-dimensional scattergram is not like those shown in FIGS. 7A to 7C. In such case, dots are distributed like as distributions of *Bacillus* and *coccus* are integrated. It is preferable to determine that a plurality of morphologic types of bacteria are contained in the measurement sample in such case. It is preferable to prevent mistakenly determining that the bacteria in the measurement sample are *Bacillus* only or *coccus* only (*Streptococcus, Staphylococcus*). In the present embodiment, in such a case, that a plurality of morphologic types of bacteria are present in the measurement sample is determined based on characteristic information other than the declination. This will be explained in the description of the specific technique of an "analysis process" below.

FIG. 8A shows the configuration of a scattergram data table Ts created in the analysis process.

The scattergram data table Ts holds the frequency of measurement data at each coordinate position on a Cartesian coordinate system having a horizontal axis (X axis) representing fluorescence intensity and a vertical axis (Y axis) representing forward scattered light intensity. For example, G11 represents the frequency of measurement data at a coordinate position (1, 1), and Gnn represents the frequency of measurement data at a coordinate position (m, n). That is, the scattergram data table Ts holds the number of bacteria plotted at each coordinate position. In FIG. 8A, the coordinates in the vertical axis and the horizontal axis are each defined as 1 to n, but the present invention is not limited thereto. For example, the set numbers of the coordinates in the horizontal axis and the vertical axis may be different from each other.

FIG. 8B illustrates a two-dimensional scattergram obtained by plotting the measurement data of bacteria as dots in a Cartesian coordinate system having a vertical axis (Y axis) representing forward scattered light intensity and a horizontal axis (X axis) representing fluorescence intensity. FIG. 8C is a schematic diagram showing the declination $\theta ij$ of a dot Pij plotted at a coordinate position (i, j) on the Cartesian coordinate system. As shown in FIG. 8C, the declination $\theta ij$ is the angle between a straight line connecting the origin O of the Cartesian coordinate system to the dot Pij, and the X axis (Y=0). It should be noted that the origin O can be changed as appropriate depending on how the 0 point of the coordinate axes is set. For example, in a case where the forward scattered light intensity and the fluorescence intensity can each be in a range of numerical values of 0 to 255, the origin may be set as (0, 0), or as (m, m) (0≤n, m≤255).

Figure 9A:
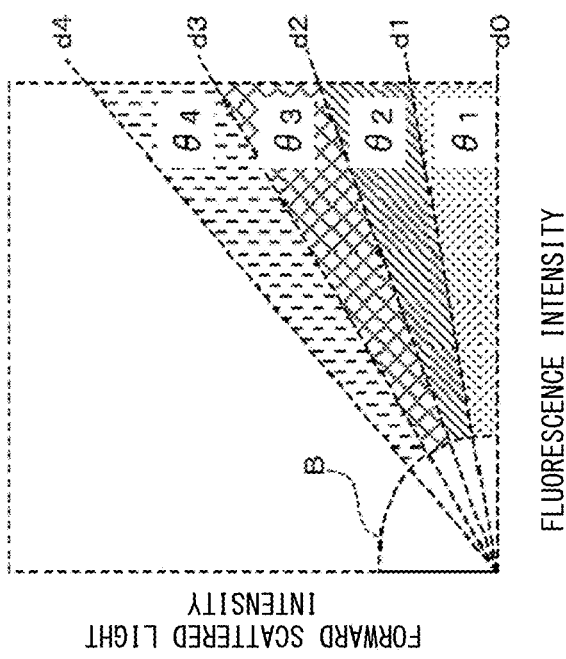
FIGS. 9A and 9B illustrate division of a scattergram according to the embodiment and regions for counting the number of bacteria on the scattergram.

FIG. 9A illustrates the concept of an angle region $\theta k$ set on a two-dimensional scattergram.

Each of straight lines d0, d1, d2, d3, d4 . . . is a straight line in a radial direction of an imaginary circle A about the origin O of a two-dimensional scattergram. The straight line d0 is identical with the horizontal axis, and each of the other straight lines has an angle γ relative to straight lines adjacent thereto as shown in FIG. 9A. Angle regions $\theta 1, \theta 2, \theta 3, \theta 4$ . . . are regions obtained by the division by the straight lines d0, d1, d2, d3, d4 . . . . γ can be set to any value, and for example, may be set to 1°, or may be set to 10°. After dividing the two-dimensional scattergram into a plurality of regions, a region B near the origin O is further excluded from the angle regions $\theta 1, \theta 2, \theta 3, \theta 4$ . . . . The region B is a region having a sector shape surrounded by a circle about the origin O and the coordinate axes.

Figure 9B:
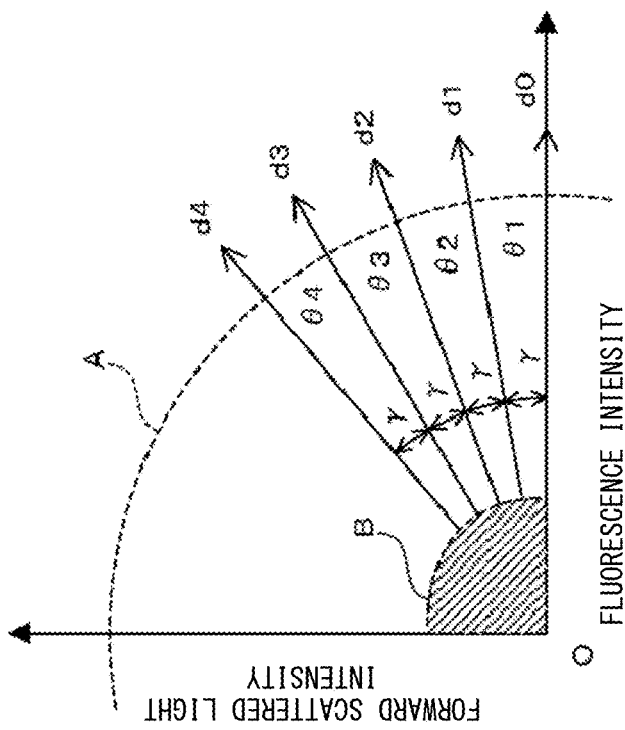

FIG. 9B shows the region obtained by excluding the region B near the origin O from the angle region $\theta k$. As shown in FIG. 9B, from the angle regions $\theta 1, \theta 2, \theta 3, \theta 4$ . . . , the region B shown in FIG. 9A is excluded. The number of bacteria contained in each of the angle regions $\theta 1, \theta 2, \theta 3, \theta 4$ . . . excluding the region B near the origin O is counted.

The reason why the region B is excluded from the angle regions $\theta 1, \theta 2, \theta 3, \theta 4$ . . . as shown in FIG. 9B is to increase the accuracy of determination of classification of urinary tract infection and determination of the morphologic types of bacteria described later. As seen from the two-dimensional scattergram in FIG. 8B, distribution of bacteria tends to be concentrated near the origin O. Therefore, in order to increase differences among count results of the angle regions $\theta 1, \theta 2, \theta 3, \theta 4$ . . . , it is preferable to exclude bacteria near the origin O from counting. Further, in the region B, compared with other regions (regions having high forward scattered light intensity and high fluorescence intensity), the regions divided by the straight lines d0, d1, d2, d3, d4 . . . are each narrow. Meanwhile, near the origin O, distributions of different morphologic types of bacteria tend to overlap each other. Therefore, in order to improve analysis accuracy, it is preferable to exclude bacteria near the origin O from counting.

For this reason, in the present embodiment, the region B near the origin O is excluded from the angle regions $\theta 1, \theta 2, \theta 3, \theta 4$ . . . in determination of classification of urinary tract infection and determination of the morphologic types of bacteria, in order to make evident the differences among the numbers of bacteria contained in the respective divided regions.

In the present embodiment, the region B having the sector shape is excluded from the angle regions $\theta 1, \theta 2, \theta 3, \theta 4$ . . . , but the region to be excluded may have another shape such as rectangle or the like. In the description below, the regions obtained by excluding the region B near the origin O from the angle region $\theta 1, \theta 2, \theta 3, \theta 4$ . . . are referred to as the angle region $\theta 1, \theta 2, \theta 3, \theta 4$ . . . , respectively.

Figures 10A, 10B, 10C:
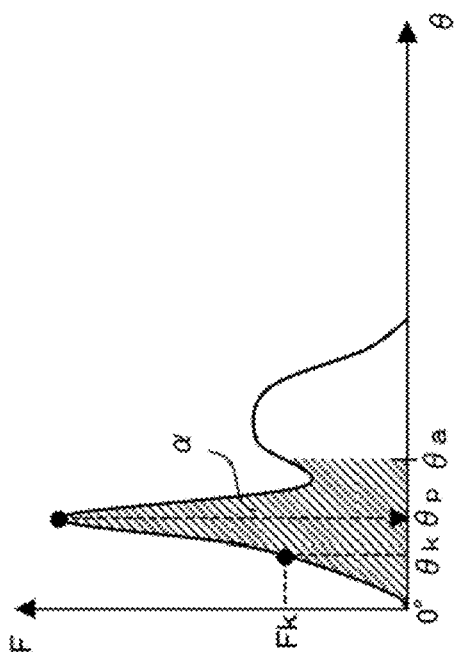
FIGS. 10A-10C illustrate histograms according to the embodiment.

FIG. 10A shows the configuration of a declination data table Td to be referred to in the analysis process. The declination data table Td holds the declination $\theta ij$ of each dot Pij shown in FIG. 8C in association with the coordinate position of the dot Pij. That is, in cells of the declination data table Td, declinations $\theta 11$ to $\theta nn$ of dots P11 to Pnn on the two-dimensional scattergram respectively corresponding to the frequencies G11 to Gnn in the scattergram data table Ts shown in FIG. 8A are stored, respectively. The declination $\theta ij$ is the angle between the straight line connecting the origin O to a dot P and the X axis (Y=0) as shown in FIG. 8C. For example, a declination $\theta 22$ of a dot P22 having coordinates (2, 2) is 45°.

FIG. 10B shows the configuration of a histogram data table Th created in the analysis process. In FIG. 10B, the leftmost row holds section orders from the horizontal axis in a case where the region from the horizontal axis to the vertical axis on the two-dimensional scattergram is sectioned into m pieces in angular directions. The middle row holds angle information (θk) of the angle region θk corresponding to each section order. The rightmost row in the histogram data table Th holds frequency data Fk regarding the frequency of appearance (the number of plots) of bacteria contained in the angle region θk.

As shown in FIG. 9B, the angle region θk is defined by two straight lines dk−1 and dk. In the angle information (θk) in the histogram data table Th shown in FIG. 10B, the angle between the horizontal axis and the straight line dk−1, which is nearer to the horizontal axis, is stored. For example, in a case where the angle range of an angle region θ2 is 10° to 20°, the cell of angle information (θ2) in the histogram data table Th stores a value of 10°.

The frequency of appearance of bacteria to be stored in a cell of the frequency data Fk is obtained by identifying declinations included in the angle range of the angle region θk, in the declination data table Td shown in FIG. 10A, identifying the coordinate position corresponding to each of the identified declinations in the scattergram data table Ts shown in FIG. 8A, and totaling the frequencies stored at the identified coordinate positions. For example, when the frequency of appearance being frequency data F2 is to be determined, first, declinations included in 10° to 20° are identified in the declination data table Td shown in FIG. 10A. In this case, a declination θ31 (θ31≈18°), a declination θ41 (θ41≈14°), and the like are identified in the declination data table Td. Next, coordinate positions (3, 1), (4, 1) and the like corresponding to the identified declinations θ31, θ41 and the like are identified in the scattergram data table Ts shown in FIG. 8A, and the frequencies G31, G41 and the like stored at the identified coordinate positions (3, 1), (4, 1) and the like are totaled, whereby the total value is obtained as the frequency data F2. In totaling the frequencies, as described above, coordinate positions included in the region B are excluded from the frequencies to be totaled.

After the histogram data table Th has been created in this manner, angle information of an angle region having the maximum frequency data is obtained as declination information θp. For example, when frequency data Fi is the maximum of all frequency data, the angle information (θi) of the angle region θi is obtained as the declination information θp.

FIG. 10C illustrates a histogram created based on the angle information (θk) and the frequency data Fk stored in the histogram data table Th shown in FIG. 10B. In FIG. 10C, the horizontal axis represents the angle information (θk) of the angle region θk, and the vertical axis represents the frequency data F corresponding to the angle region θk. In this example, of two peaks in the histogram, the angle information corresponding to the left peak is obtained as the declination information θp.

The declination information θp obtained in this manner corresponds to the inclination angle of the straight line shown in any of FIGS. 7A to 7C relative to the horizontal axis. The declination information θp is a parameter indicative of a characteristic of a distribution pattern of particles on a two-dimensional scattergram. In more detail, the declination information θp indicates the position where particles are concentrated on the two-dimensional scattergram, and is a representative value of relations between the surface area and the degree of staining of each bacterium contained in the measurement sample. By comparing the declination information θp with a predetermined threshold value, the morphologic type of bacteria contained in the measurement sample can be determined.

In a case where a plurality of morphologic types of bacteria are present in the measurement sample, it is preferable to correctly determine that a plurality of morphologic types of bacteria are present. In the present embodiment, for this determination, a proportion α of the frequency in a low angle region θL relative to the frequency in the entire angle region (θ1 to θm) is further used. Here, the low angle region θL is an angle region included in the range of 0° to θa as shown in FIG. 10C. For example, when the angle regions θ1 and θ2 are set as the low angle region θL, the proportion of a value FL obtained by adding frequency data F1 and frequency data F2, relative to a total value FA of frequency data F1 to Fm is calculated as the proportion α. The proportion α is obtained by the following formula.

$$\alpha = (FL/FA) \times 100 \qquad (1)$$

θa which defines the low angle region θL can be set to, for example, 0°<θa<30°. More preferably, θa can be set to 0°<θa<20°.

In the histogram shown in FIG. 10C, the hatched region corresponds to the low angle region θL. The proportion of the frequency of this region relative to the frequency of the entire region is the proportion α.

The proportion α is a parameter indicative of the relation between the distribution state in the entire histogram in the angle range of 0° to 90° and the distribution state in a partial angle range thereof. The proportion α in the present embodiment is a value indicative of the proportion of the number of particles in the low angle region θL relative to the number of particles in the entire angle range. That is, it is suggested that the greater the value of the proportion α is, the more localized the particles are in the low angle region, in the scattergram. That is, it is seen that there is a high possibility that bacilli alone are present. On the other hand, if the value of the proportion α is small, it is suggested that the particles are dispersed in a wide range from a low angle to a high angle.

The morphologic type of the bacteria contained in the measurement sample, *Bacillus*, coccus (*Streptococcus*, *Staphylococcus*), or a mixed-type, is determined based on a combination of the proportion α and the declination information θp.

Figure 11A:
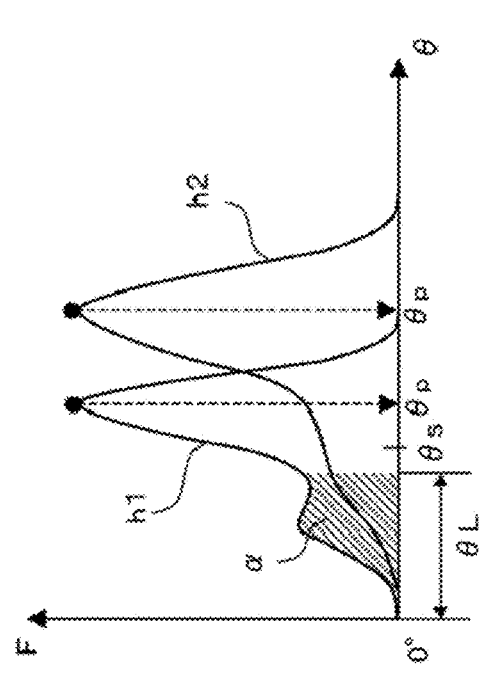
FIGS. 11A-11D schematically show feature spaces for determining the morphologic types of bacteria according to the embodiment.

FIG. 11A is a schematic diagram showing a feature space for determining the morphologic type of bacteria contained in a specimen. In FIG. 11A, the horizontal axis represents the magnitude of the proportion α and the vertical axis represents the magnitude of the declination information θp.

As shown in FIG. 11A, in the feature space, a threshold angle θs and a threshold value αs are set on the vertical axis and the horizontal axis, respectively. The feature space is sectioned into determination regions S1 to S3 by the threshold angle θs and the threshold value αs. As described above, based on which the measurement result to of the specimen belongs to among the determination regions S1 to S3, the morphologic type of bacteria contained in the measurement sample is determined.

Figure 11B:
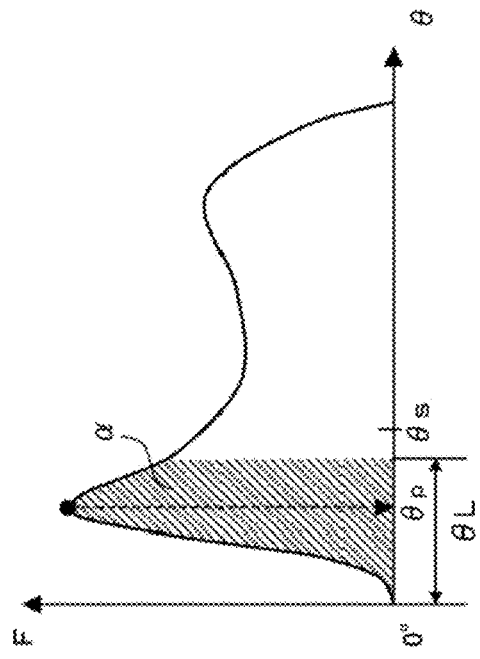
Figure 11C:
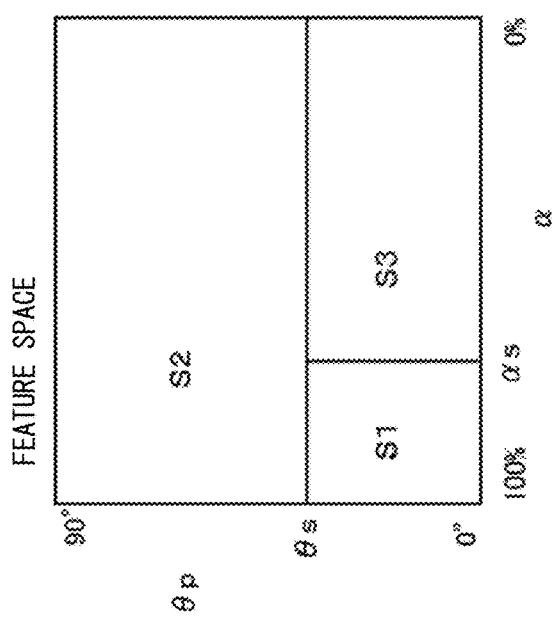
Figure 11D:
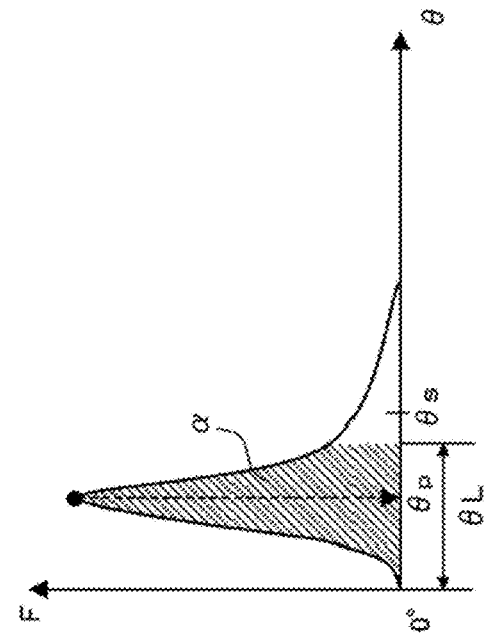

FIG. 11B illustrates histograms when cocci (*Streptococci*, *Staphylococci*) are mainly contained in a measurement sample. FIG. 11C illustrates a histogram when bacilli are mainly contained in a measurement sample. FIG. 11D illustrates a histogram when a plurality of morphologic types of bacteria are contained in a measurement sample. FIG. 11B shows a histogram h1 when *Streptococci* are contained in a measurement sample and a histogram h2 when *Staphylococci* are contained in a measurement sample.

As shown in FIG. 11C, when bacilli are mainly contained in a measurement sample, in the histogram, a peak emerges in a range of angle less than or equal to the threshold angle θs, and the frequency of appearance of data tends to be concentrated on the low angle side. Therefore, as shown in FIG. 11A, the determination region S1 corresponding to *Bacillus* is set to a region in which the declination information θp is less than or equal to the threshold angle θs and the proportion α is greater than or equal to the threshold value αs.

As shown in FIG. 11D, when a plurality of morphologic types of bacteria are present in a measurement sample, in the histogram, a peak emerges in a range of angle less than or equal to the threshold angle θs, and the frequency of appearance of data tends to be distributed in a gently sloping shape from a low angle to a high angle. Therefore, as shown in FIG. 11A, the determination region S3 corresponding to a mixed-type (a plurality of morphologic types of bacteria are present) is set to a region in which the declination information θp is less than or equal to the threshold angle θs and the proportion α is less than the threshold value αs.

As shown in FIG. 11B, when cocci (*Streptococci, Staphylococci*) are mainly contained in a measurement sample, in the histogram, peaks emerge in a range of angle greater than the threshold angle θs. Therefore, as shown in FIG. 11A, the determination region S2 corresponding to cocci (*Streptococci, Staphylococci*) is set to a region in which the declination information θp is greater than the threshold angle θs.

The morphologic type of the bacteria contained in a measurement sample is determined based on to which the measurement sample belongs among the determination regions in the feature space shown in FIG. 11A defined by the combination of the declination information θp and the proportion α. That is, in a case where the combination of the declination information θp and the proportion α of a measurement sample belongs to the determination region S1, it is determined that the morphologic type of the bacteria contained in the measurement sample is *Bacillus*. In a case where the combination belongs to the determination region S2, the morphologic type of the bacteria contained in the measurement sample is determined as *coccus (Streptococcus, Staphylococcus)*. In a case where the combination belongs to the determination region S3, it is determined that the morphologic type of the bacteria contained in the measurement sample is a mixed-type.

It should be noted that the threshold angle θs and the threshold value αs are set such that a high determination accuracy can be obtained, in consideration of characteristics and the like of the measurement apparatus. Similarly, the low angle region θL for obtaining the proportion α is also set such that a high determination accuracy can be obtained, in consideration of characteristics and the like of the measurement apparatus. The threshold angle θs, the threshold value αs, and the low angle region θL are set as default or may be adjustable as appropriate by an operator.

Further, in the present embodiment, the morphologic type of bacteria is determined based on the combination of the declination information θp and the proportion α. Therefore, even if two or more peaks appears in the histogram, the morphologic type of bacteria can be appropriately determined. For example, in the histogram h1 shown in FIG. 11B, peaks emerge at two angles. This is caused not by the presence of bacilli and cocci in the measurement sample. Instead, the small peak has emerged in a low angle range, due to the distribution state of dots in the two-dimensional scattergram. In such case, according to the conventional technique of determination of the morphologic type of bacteria described in U.S. Patent application publication No. 2010-0047856 in which only a peak angle and the number of peaks are used, determination may be erroneously made that the morphologic type of the bacteria contained in the measurement sample is a mixed-type. In contrast, according to the present embodiment, since the angle of highest peak θp is higher than the threshold angle θs and the proportion α is small, it can be appropriately determined that the morphologic type of bacteria contained in the measurement sample is cocci alone.

Also, there may be a case where the morphologic type of bacteria contained in the measurement sample is a mixed-type but only one peak emerges, or a case where the morphologic type of bacteria contained in the measurement sample is *Bacillus* alone but a plurality of peaks emerge.

Figure 12B:
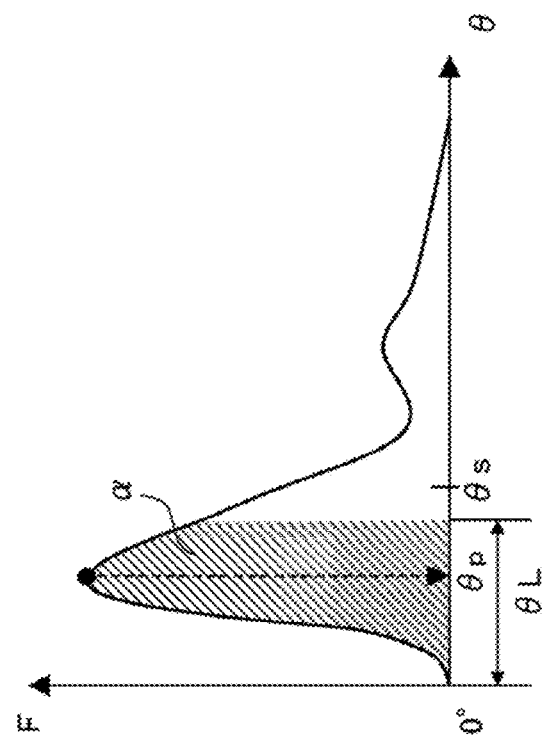
FIGS. 12A and 12B illustrate histograms according to the embodiment.
Figure 12A:
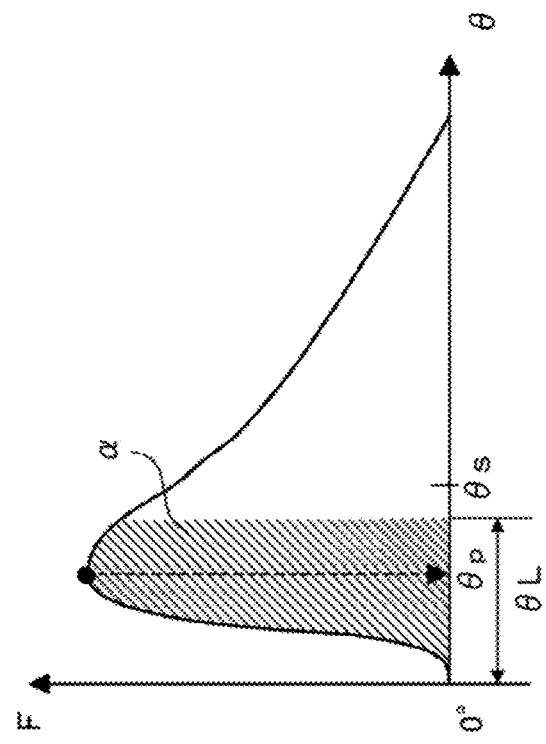

FIG. 12A illustrates a histogram when a plurality of morphologic types of bacteria are present in a measurement sample. FIG. 12B illustrates a histogram when bacilli are mainly contained in a measurement sample.

*Streptococci* include various types having different chain lengths. Therefore, as shown in FIG. 12A, in a case where the peak indicating *Bacillus* and the peak indicating coccus overlap each other, although the morphologic type of bacteria is a mixed-type, a histogram which has a gently sloping waveform as a whole with only one peak emerging may be obtained. In this case, according to the conventional determination technique described in U.S. Patent application publication No. 2010-0047856, determination may be erroneously made that the morphologic type of bacteria contained in the measurement sample is *Bacillus* alone. In contrast, according to the present embodiment, since the proportion α is smaller than the threshold value αs, it can be appropriately determined that the morphologic type of bacteria contained in the measurement sample is a mixed-type.

Even in a case where the morphologic type of bacteria contained in a measurement sample is *Bacillus* alone, if two or more bacilli simultaneously pass through the flow cell 203c, a plurality of bacilli gather to form a large particle. Thus, as shown in FIG. 12B, the second peak may accidentally emerge in a high angle range. In this case, according to the conventional determination technique described in U.S. Patent application publication No. 2010-0047856, determination may be erroneously made that the morphologic type of bacteria contained in the measurement sample is a mixed-type. In contrast, according to the present embodiment, since the proportion α is greater than or equal to the threshold value αs, it can be appropriately determined that the morphologic type of bacteria contained in the measurement sample is *Bacillus* alone.

Figure 13:
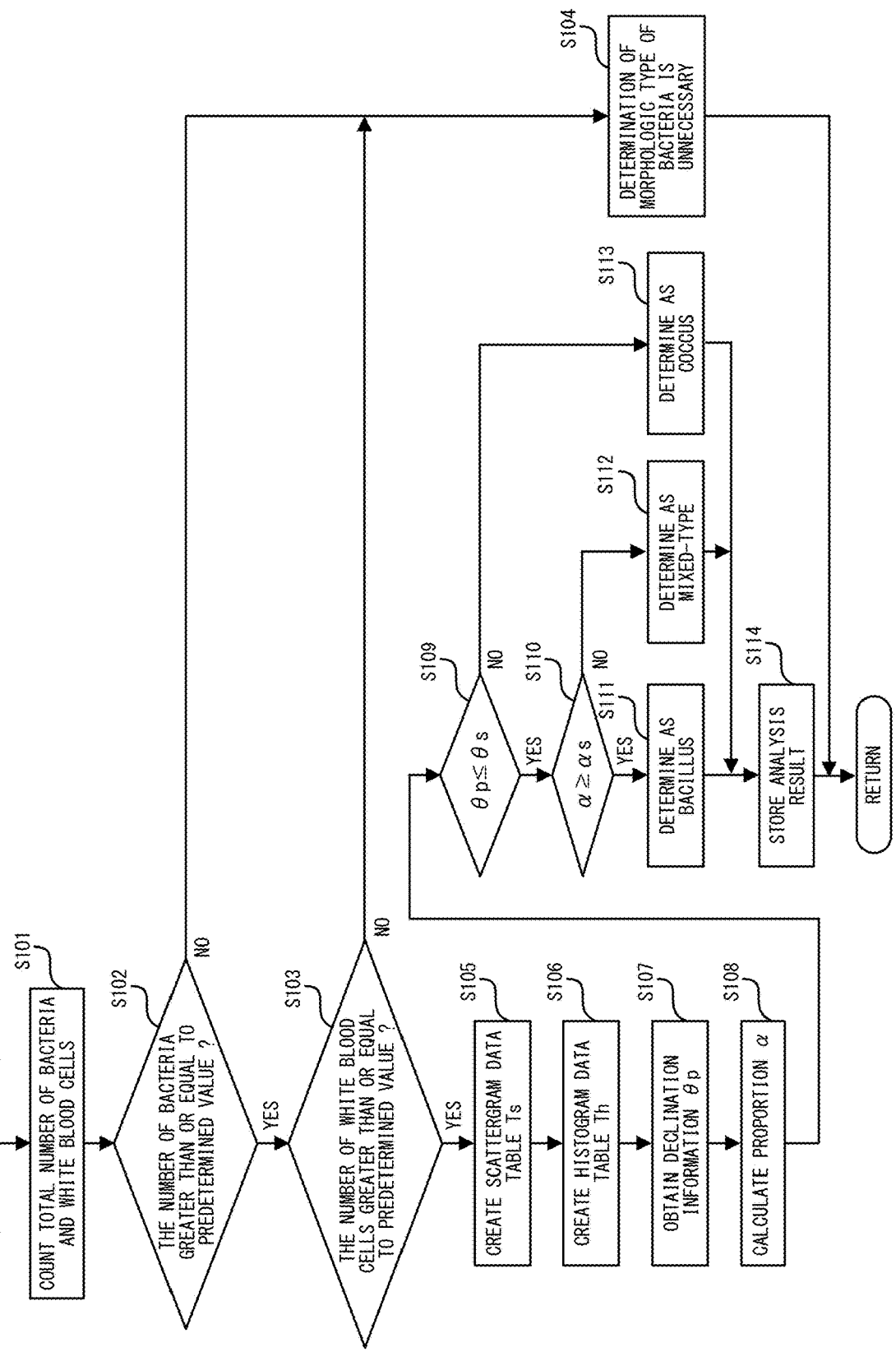
FIG. 13 is a flow chart showing the analysis process according to the embodiment.

FIG. 13 is a process flow chart of the "analysis process" of S14 in FIGS. 6A and 6B.

First, the CPU 301 reads out measurement data from the hard disk 304 onto the RAM 303, and counts, based on the read measurement data, the total number of bacteria and the total number of white blood cells contained in the measurement sample (S101). The total number of bacteria and the total number of white blood cells are respectively counted based on measurement data obtained from samples separately prepared by the component units shown in FIG. 3. In the present embodiment, as shown in FIG. 3, the sample for counting bacteria and the sample for counting white blood cells are separately prepared, but a sample prepared for counting bacteria may also be used for counting white blood cells. In this case, the detection sensitivities for forward scattered light intensity and fluorescence intensity are adjusted to sensitivities appropriate therefor, at the time of counting bacteria and at the time of counting white blood cells, respectively.

Subsequently, the CPU 301 determines whether the number of bacteria contained in the measurement sample is greater than or equal to a predetermined value (S102). That is, from the total number of bacteria counted in S101, the number of bacteria contained in 1 μL of the measurement sample is obtained, and whether this number of bacteria is greater than or equal to a predetermined value is determined. In order to perform analysis for determining the morphologic type of bacteria in the present embodiment, a certain number of bacteria are required. In the present embodiment, the predetermined value to be used in the determination in S102 is about 100 for 1 μL of the measurement sample.

In a case where the number of bacteria contained in the measurement sample is greater than or equal to the predetermined value (S102: YES), the CPU 301 further determines whether the number of white blood cells contained in the measurement sample is greater than or equal to a predetermined value (S103). That is, from the total number of white blood cells counted in S101, the number of white blood cells contained in 1 μL of the measurement sample is obtained, and whether this number of white blood cells is greater than or equal to a predetermined value is determined. In the present embodiment, the predetermined value to be used in the determination in S103 is, for example, about 10 for 1 μL of the measurement sample.

As described above, in the present embodiment, as factors for determining whether to start analysis for determining the morphologic type of bacteria, the total number of white blood cells is used in addition to the total number of bacteria. Accordingly, analysis for determining the morphologic type of bacteria can be performed only on a specimen for which urinary tract infection is suspected.

Upon determining that the number of bacteria contained in the measurement sample is smaller than the predetermined value (S102: NO), or upon determining that the number of white blood cells contained in the measurement sample is smaller than the predetermined value (S103: NO), the CPU 301 determines that determination of the morphologic type of bacteria is not necessary (S104), and ends the process. On the other hand, upon determining that the number of bacteria contained in the measurement sample is greater than or equal to the predetermined value (S102: YES), and then determining that the number of white blood cells contained in the measurement sample is greater than or equal to the predetermined value (S103: YES), the CPU 301 advances the process to S105.

In S105, the CPU 301 creates a scattergram data table Ts shown in FIG. 8A based on the measurement data. Further, based on the created scattergram data table Ts, the CPU 301 creates a histogram data table Th shown in FIG. 10B (S106).

Next, by using the created histogram data table Th, the CPU 301 extracts an angle region having the maximum frequency data as described above, and obtains declination information θp corresponding to that angle region (S107). Further, by using the histogram data table Th, the CPU 301 calculates a proportion a of the frequency of the low angle region θL relative to the frequency of the entire angle region (S108) as described above.

When having calculated the declination information θp and the proportion α, the CPU 301 determines to which of the determination regions S1 to S3 of the feature space shown in FIG. 11A, the above characteristic information belongs (S109, S110). Accordingly, the morphologic type of bacteria contained in the specimen is determined, and the specimen is provided with a flag regarding morphological characteristics of bacteria, in accordance with the determination result. Specifically, when the declination information θp is less than or equal to the threshold angle θs (S109: YES) and when the proportion α is greater than or equal to the threshold value αs (S110: YES), that is, when the above characteristic information is included in the determination region S1 of the feature space, the CPU 301 determines that the bacteria contained in the measurement sample are mainly bacilli (S111). This specimen is provided with a flag "*Bacillus*" as the flag regarding morphological characteristics of bacteria. Further, when the declination information θp is less than or equal to the threshold angle θs (S109: YES), and when the proportion α is less than the threshold value as (S110: NO), that is, when the above characteristic information is included in the determination region S3 of the feature space, the CPU 301 determines that a plurality of morphologic types of bacteria are present in the measurement sample (S112). This specimen is provided with a flag "mix" as the flag regarding morphological characteristics of bacteria. Further, when the declination information θp exceeds the threshold angle θs (S109: NO), that is, when the above characteristic information is included in the determination region S2 of the feature space, the CPU 301 determines that the bacteria contained in the measurement sample are mainly cocci (*Streptococci* or *Staphylococci*) (S113). This specimen is provided with a flag "coccus" as the flag regarding morphological characteristics of bacteria.

In the present embodiment, through the determination in S109, whether the bacteria contained in the specimen is cocci or not is determined. However, whether the type of cocci is *Streptococcus* or *Staphylococcus* may be further finely determined. In this case, a second threshold angle θs2 is set for dividing the determination region S2 of the feature space into two. The second threshold angle θs2 is set to be greater than the declination obtained in the case of *Streptococcus* and smaller than the declination obtained in the case of *Staphylococcus*. For example, the second threshold angle θs2 is set to be an angle between the declination information θp of the histogram h1 and the declination information θp of the histogram h2 in FIG. 11B. Accordingly, the type of cocci can be further finely determined.

Then, the CPU 301 stores, in the hard disk 304, an analysis result including a determination result regarding the presence/absence of urinary tract infection and the flag regarding morphological characteristics of bacteria obtained as described above (S114), and ends the analysis process. Then, in S15 in FIG. 6B, the CPU 301 creates a display screen for displaying the obtained analysis result, and causes the display unit 320 to display the created display screen.

Figure 14:
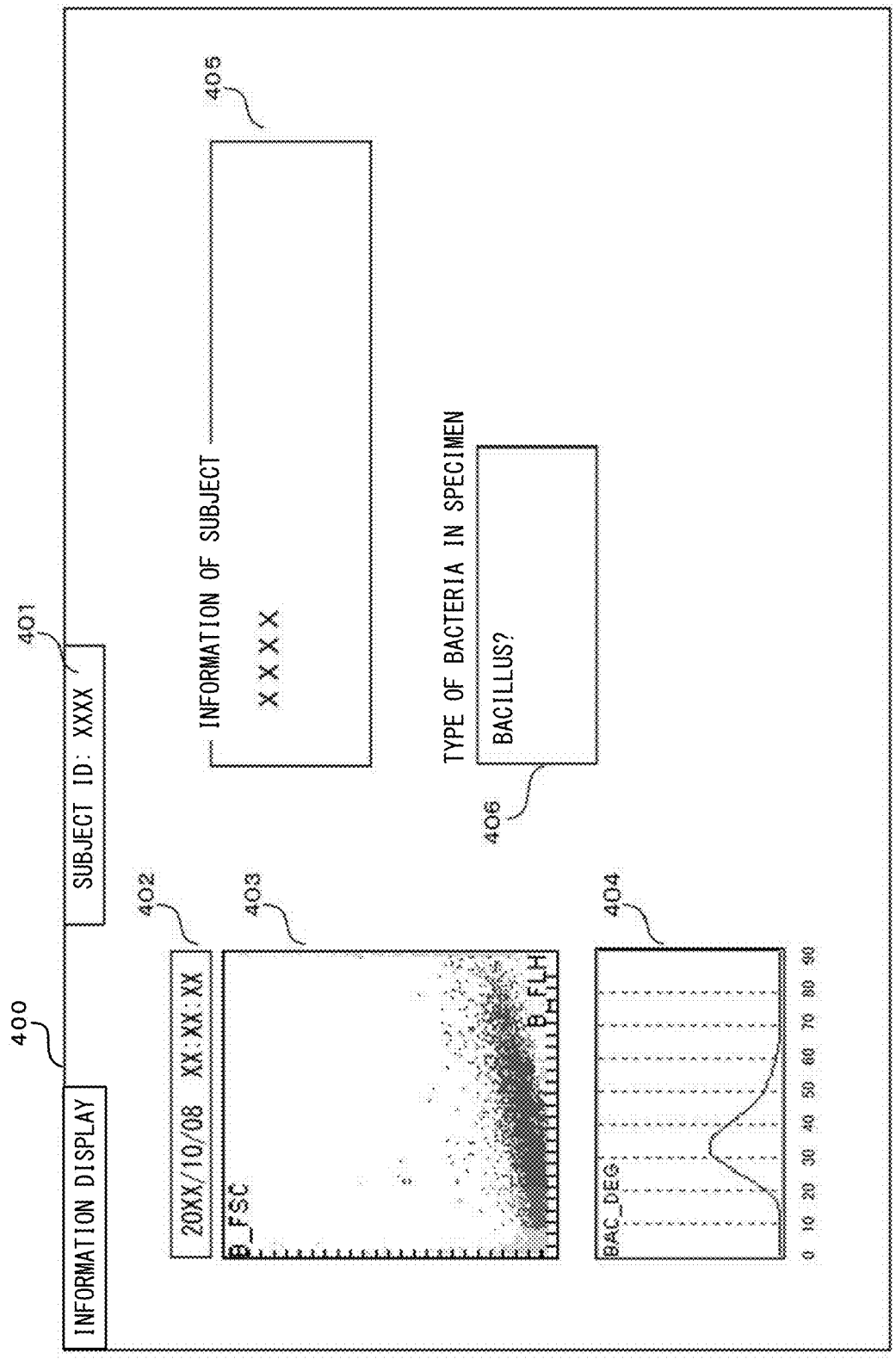
FIG. 14 illustrates an information displaying screen displayed on a display unit of the information processing apparatus according to the embodiment.

FIG. 14 illustrates an information displaying screen 400 to be displayed on the display unit 320 of the information processing apparatus 3. The information displaying screen 400 is displayed in accordance with S15 in FIGS. 6A and 6B.

The information displaying screen 400 includes a subject ID region 401, a measurement date and time region 402, a scattergram region 403, a histogram region 404, a subject information region 405, and a bacteria information region 406.

In the subject ID region 401, a subject ID which identifies a subject from whom the specimen being the source of this analysis was collected is displayed. In the measurement date and time region 402, a measurement date and time when this measurement was performed is displayed. In the scattergram region 403, a two-dimensional scattergram corresponding to FIG. 8B obtained through this measurement is displayed. In the histogram region 404, a histogram corresponding to FIG. 10C obtained based on the scattergram displayed in the scattergram region 403 is displayed.

In the subject information region 405, the name of the subject corresponding to the subject ID, the doctor in charge, comments from the doctor in charge, and the like are displayed. In addition to this, information regarding drugs administered to this subject may be inputted via the input unit 310 (see FIG. 5), to be displayed in the subject information region 405.

In the bacteria information region 406, the flag regarding morphological characteristics of bacteria provided to the specimen in the analysis process shown in FIG. 13 or a message corresponding to the flag is displayed. For example, when the flag "*Bacillus*" has been provided to the specimen (S111), "*BACILLUS?*" is displayed in the bacteria information region 406. When the flag "mix" has been provided to the specimen (S112), "MIX?" or "*BACILLUS/COCCUS?*" is displayed in the bacteria information region 406. When the flag "coccus" has been provided to the specimen (S113), "*COCCUS?*" is displayed in the bacteria information region 406. It should be noted that the "?" added to the end of the display content in the bacteria information region 406 means that there is a high possibility that this specimen contains bacteria of the morphologic type indicated by the display content. When the morphologic type of bacteria has not been determined or when the morphologic type of bacteria could not be determined, the bacteria information region 406 remains blank or "UNKNOWN" is displayed in the bacteria information region 406.

The information displaying screen 400 may further include a region in which whether urinary tract infection is suspected is displayed. In this case, "URINARY TRACT INFECTION?" is displayed. It should be noted that when determination of S104 in FIG. 13 has been performed, nothing is displayed in this region.

FIG. 15A is a table showing results of determination of the morphologic type of bacteria according to the present embodiment performed on 85 urinary tract infection specimens. FIG. 15B is a table showing results of determination according to the prior art described in U.S. Patent application publication No. 2010-0047856 above performed on 85 urinary tract infection specimens. References are determination results from visual observation of Gram stain samples (*Bacillus*: 64 specimens, coccus: 11 specimens, mixed-type (mix of *Bacillus* and coccus): 10 specimens). The concordance rate, the sensitivity, and the PPV (positive predictive value) therebetween are shown.

In the algorithm described in U.S. Patent application publication No. 2010-0047856 above, with respect to a scattergram using, as parameters, forward scattered light intensity and fluorescence intensity of bacteria contained in a specimen, the angle of each bacterium relative to the origin is detected. Then, in a histogram of the angle and the number of bacteria, based on the angle where a peak emerges, the morphologic type of bacteria is determined. In the determination of the morphologic type of bacteria, the angle region that includes the peak and the morphologic type of bacteria are associated with each other. Here, a low angle region (greater than or equal to 0 degree and less than or equal to 25 degrees) is allocated to *Bacillus*, a medium angle region (greater than 25 degrees and less than or equal to 45 degrees) is allocated to *Streptococcus*, and a high angle region (greater than 45 degrees and less than or equal to 80 degrees) is allocated to *Staphylococcus*. In the determination in FIG. 15B, when a peak is included in the angle region of *Streptococcus* or *Staphylococcus*, it is determined as "coccus", and when two peaks are included in the angle region of *Bacillus* and the angle region of coccus (*Streptococcus, Staphylococcus*), respectively, it is determined as "mix".

With reference to FIG. 15A, determination results according to the present embodiment will be described.

Among 64 specimens determined as *Bacillus* in visual observation, 50 specimens were determined as *Bacillus* by the determination technique of the present embodiment. Moreover, among 11 specimens determined as coccus in visual observation, 5 specimens were determined as coccus by the determination technique of the present embodiment. Furthermore, among 10 specimens determined as the mixed-type (mix) in visual observation, 5 specimens were determined as the mixed-type (mix) by the determination technique of the present embodiment.

On the other hand, among 55 specimens determined as *Bacillus* in the determination results by the present embodiment, 50 specimens were determined as *Bacillus* also in visual observation. Moreover, among 8 specimens determined as coccus in the determination results by the present embodiment, 5 specimens were determined as coccus also in visual observation. Furthermore, among 22 specimens determined as the mixed-type (mix) in the determination results by the present embodiment, 5 specimens were determined as the mixed-type (mix) also in visual observation.

From the above, the concordance rate as a whole between the visual observation and the determination technique of the present embodiment was 70.6% (60/85), and thus, it has been clarified that a high determination accuracy was obtained. More specifically, the sensitivity to *Bacillus* was 78.1% (50/64), the PPV for *Bacillus* was 90.9% (50/55), the sensitivity to coccus was 45.5% (5/11), the PPV for coccus was 62.5% (5/8), the sensitivity to the mixed-type of *Bacillus* and coccus was 50.0% (5/10), and the PPV therefor was 22.7% (5/22).

With reference to FIG. 15B, determination results by the prior art will be described.

Among 64 specimens determined as *Bacillus* in visual observation, 48 specimens were determined as *Bacillus* by the determination technique of the prior art. Moreover, among 11 specimens determined as coccus in visual observation, 6 specimens were determined as coccus by the determination technique of the prior art. Furthermore, among 10 specimens determined as the mixed-type (mix) in visual observation, 0 specimens were determined as the mixed-type (mix) by the determination technique of the prior art.

On the other hand, among 56 specimens determined as *Bacillus* in the determination results by the prior art, 48 specimens were determined as *Bacillus* also in visual observation. Moreover, among 15 specimens determined as coccus in the determination results by the prior art, 6 specimens were determined as coccus also in visual observation. Furthermore, among 14 specimens determined as the mixed-type (mix) in the determination results by the prior art, 0 specimens were determined as the mixed-type (mix) also in visual observation.

From the above, the concordance rate as a whole between the visual observation and the determination technique of the prior art was 63.5% (54/85). More specifically, the sensitivity to *Bacillus* was 75.0% (48/64), the PPV for *Bacillus* was 85.7% (48/56), the sensitivity to coccus was 54.5% (6/11), the PPV for coccus was 40.0% (6/15), the sensitivity to the mixed-type of *Bacillus* and coccus was 0.0% (0/10), and the PPV therefor was 0.0% (0/14).

As described above, it is seen that, in the determination technique according to the present embodiment, the PPV for *Bacillus* and the PPV for coccus were good compared with those of the determination technique of the prior art, and in particular, the sensitivity to and the PPV for the mixed-type were very good. Further, as a whole, the concordance rate of a little greater than 70% was obtained, and thus, it is seen that the morphologic type of bacteria can be accurately determined by the determination technique according to the present embodiment. Thus, specimens containing bacilli only, specimens containing cocci only, and specimens containing both can be accurately determined, respectively, and thus, information for selecting an appropriate antibacterial agent can be provided.

As described above, according to the present embodiment, as shown in FIG. 11A, the morphologic type of bacteria is determined based on the relation between the declination information θp and the proportion α. Therefore, as shown in FIG. 11B and FIG. 12B, even in a case where a plurality of peaks emerge, that the morphologic type of bacteria is *Bacillus* or coccus alone can be appropriately determined. Moreover, as shown in FIG. 12A, even in a case where only one peak emerges, that the morphologic type of bacteria is the mixed-type can be appropriately determined. Thus, compared with the determination technique of the morphologic type of bacteria based on only a peak angle and the number of emergences of peak angles described in U.S. Patent application publication No. 2010-0047856 above, the morphologic type of bacteria can be accurately determined.

According to the present embodiment, as shown in FIG. 11A, by use of the feature space defined into the determination regions S1 to S3, the morphologic type of bacteria is determined based on which determination region includes the combination of the declination information θp and the proportion α. Therefore, the morphologic type of bacteria contained in the specimen can be determined through a simple process.

Moreover, according to the present embodiment, in a case where the declination information θp and the proportion α are included in the determination region S1, the morphologic type of bacteria contained in the specimen is determined as *Bacillus*, in a case where the declination information θp and the proportion α are included in the determination region S2, the morphologic type of bacteria contained in the specimen is determined as coccus, and in a case where the declination information θp and the proportion α are included in the determination region S3, the morphologic type of bacteria contained in the specimen is determined as the mixed-type of *Bacillus* and coccus. Accordingly, as shown in FIGS. 15A and 15B, whether the morphologic type of bacteria contained in the specimen is *Bacillus*, coccus, or the mixed-type can be accurately determined.

According to the present embodiment, as shown in S102 in FIG. 13, in a case where the number of bacteria contained in the measurement sample is not greater than or equal to the predetermined value, it is determined that determination of the morphologic type of bacteria is not necessary, and the process of determining the morphologic type of bacteria is not performed. Therefore, unnecessary determination of the morphologic type of bacteria can be prevented from being performed, and also a determination result of a low accuracy based on an insufficient measurement sample can be prevented from being provided to a user.

According to the present embodiment, as shown in S103 in FIG. 13, in addition to the number of bacteria, the number of white blood cells contained in the measurement sample is referred to, whereby the necessity/unnecessity of determination of the morphologic type of bacteria is determined. Therefore, compared with a case where the necessity/unnecessity of determination of the morphologic type of bacteria is determined based on only the number of bacteria, the necessity/unnecessity of determination of the morphologic type of bacteria can be further appropriately determined. Thus, a determination result of bacteria of higher accuracy can be obtained.

According to the present embodiment, since the morphologic type of bacteria of a urine specimen is determined, effective administration and treatment can be performed timely.

Although an embodiment of the present invention has been described above, the present invention is not limited to the above embodiment, and various changes can be made to the embodiment of present invention.

For example, although urine is exemplified as a measurement subject in the above embodiment, a body fluid other than blood and urine can be a measurement subject. That is, the present invention can also be applied to a specimen test apparatus which tests a body fluid. Here, a "body fluid" means the celomic fluid present in a celom. Specifically, the body fluid means cerebrospinal fluid (spinal fluid, CSF: fluid filled in the cerebral ventricle and the subarachnoid space), pleural effusion (pleural fluid, PE: fluid in the pleural cavity), ascitic fluid (fluid in the peritoneal cavity), pericardial effusion (fluid in the pericardial cavity), synovial fluid (joint fluid: fluid present in joints, the synovial bursa, or the peritenon), and the like. Moreover, a dialysate for continuous ambulatory peritoneal dialysis (CAPD) and a peritoneal cavity cleaning solution are included in the body fluid.

In the above embodiment, two types of optical information of forward scattered light intensity and fluorescence intensity are obtained, and the distribution of particles in a coordinate plane using these two intensities as two axes is analyzed, whereby the morphologic type of bacteria is determined, and the coordinate plane (scattergram) used in the analysis is displayed on the information displaying screen (FIG. 14). However, the particle distribution chart to be displayed on the information displaying screen does not necessarily have the same coordinate plane as that used in the analysis. For example, separately from the coordinate plane to be used in determining the morphologic type of bacteria, based on three types of optical information (for example, forward scattered light intensity, side scattered light intensity, and fluorescence intensity) obtained from each particle, a three-dimensional scattergram using these three parameters as axes may be generated to be displayed on the information displaying screen. Alternatively, a particle distribution chart of a three-dimensional coordinate space is generated, and then, a certain plane in the coordinate space is subjected to the analysis according to the present embodiment, whereby determination of the morphologic type of bacteria may be performed. In any case, it is essential to analyze the particle distribution on a coordinate plane having two types of optical information as axes. As long as such a step is taken, such a determination method is included in the range of the bacteria analyzing method according to the present invention.

In the above embodiment, as shown in FIG. 11A, the feature space is defined into simple rectangular shapes. However, in order to further improve the concordance rate and the predictive value, the determination regions in the feature space are preferably optimized based on collected data results.

Figure 16A:
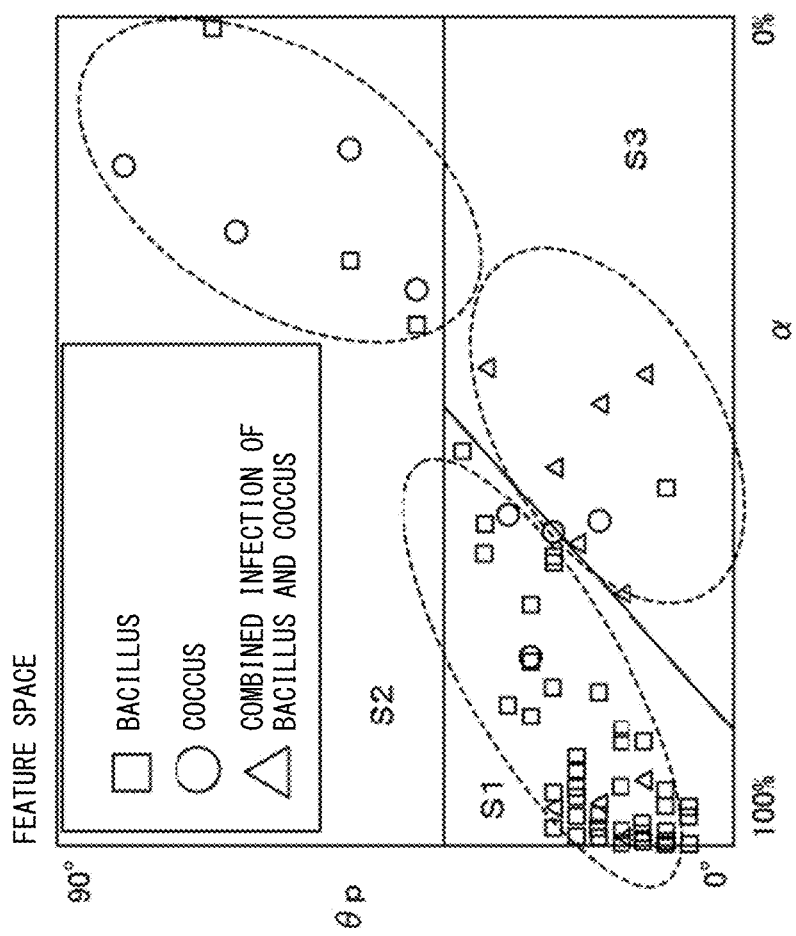
FIGS. 16A and 16B show schematic diagrams of a feature space for determining the morphologic type of bacteria according to a modification.
Figure 16B:
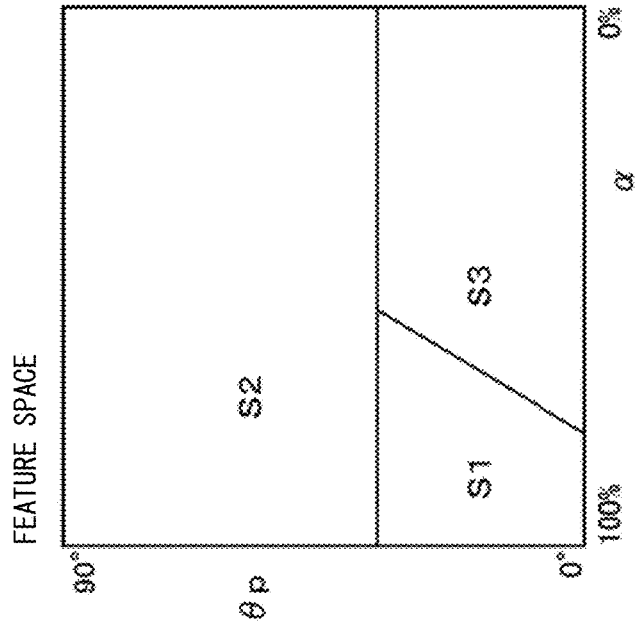

FIG. 16A illustrates a feature space according to a modification. FIG. 16B illustrates the feature space according to the modification in which determination results of the morphologic type of bacteria are distributed.

As shown in FIG. 16A, in the present modification, the feature space is defined such that the border line between the determination region S1 and the determination region S3 is inclined. Accordingly, as shown in FIG. 16B, determination of the morphologic type of bacteria can be made more appropriate.

In the above embodiment, as shown in FIG. 11A, the feature space is defined into three regions of the determination regions S1 to S3, but the determination regions S2 and S3 may be integrated into one determination region.

Figure 17:
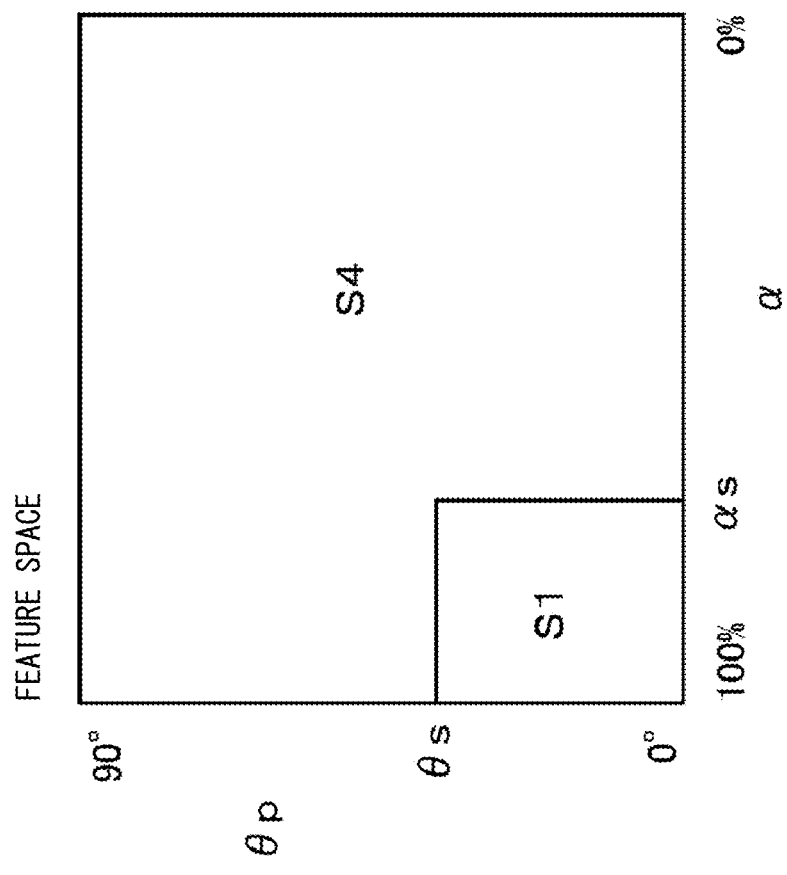
FIG. 17 is a schematic diagram showing a feature space for determining the morphologic type of bacteria according to a modification.

FIG. 17 is a schematic diagram showing the feature space for determining the morphologic type of bacteria contained in a specimen according to a modification.

As shown in FIG. 17, in the present modification, depending on which of the determination regions S1 or S4 includes the measurement result of a specimen, whether the morphologic type of bacteria contained in the measurement sample is *Bacillus* alone or other morphologic type (coccus or mix) than *Bacillus* is determined.

In this case, the specimen is provided with, as the flag regarding morphological characteristics of bacteria, either one of two morphologic types, i.e., "*Bacillus*" and "coccus or mix". Although the number of morphologic types of flags is less than in the embodiment described above, by provision of the two morphologic types of flags, it is possible to provide information to be used for determining whether to select an antibacterial agent to which *Bacillus* is susceptible, or an antibacterial agent having a broad spectrum to which both *Bacillus* and coccus are susceptible.

FIG. 18A shows a feature space obtained by further modifying the feature space in FIG. 17. FIG. 18B is a table showing determination results of the morphologic type of bacteria obtained based on the present modification.

Among 64 specimens determined as *Bacillus* in visual observation, 52 specimens were determined as *Bacillus* by the determination technique of the present modification. Moreover, among 21 specimens determined as coccus or the mixed-type (mix) in visual observation, 15 specimens were determined as coccus or the mixed-type (mix) by the determination technique of the present modification.

On the other hand, among 58 specimens determined as *Bacillus* in the determination results by the present modification, 52 specimens were determined as *Bacillus* also in visual observation. Moreover, among 27 specimens determined as coccus or the mixed-type (mix) in the determination results by the present modification, 15 specimens were determined as coccus or the mixed-type (mix) also in visual observation.

From the above, the concordance rate as a whole between the visual observation and the determination technique of the present modification was 78.8% (67/85), and thus, it has been clarified that a higher determination accuracy was obtained. The sensitivity to *Bacillus* was 81.3% (52/64), the PPV for *Bacillus* was 89.7% (52/58), the sensitivity to coccus or the mixed-type (mix) was 71.4% (15/21), and the PPV for coccus or the mixed-type (mix) was 55.6% (15/27), which means that coccus or the mixed-type was determined more accurately.

The determination regions set in the feature space may have various shapes such as an elliptical shape, other than these. In accordance with the morphologic types of bacteria to be determined, the position, the number, and the like of regions can also be changed as appropriate.

In the above embodiment, as shown in FIG. 11A, based on which of the determination regions S1 to S3 includes the measurement result of a specimen, the morphologic type of bacteria contained in the measurement sample is determined. However, classification of which region includes the measurement result of the specimen is performed once, and then the result included in a certain region is further classified, whereby the morphologic type of bacteria contained in the measurement sample may be determined. Moreover, classification of which region includes the measurement result of the specimen is performed once, and further, this classification is corrected in accordance with a predetermined criterion, whereby the morphologic type of bacteria contained in the measurement sample may be determined.

When proliferating, bacilli are less likely to form a large aggregate, unlike *Staphylococci* or *Streptococci*. Therefore, usually, in the case of *Bacillus*, as shown in FIG. 7A, most dots tend to be distributed in a lower region on a two-dimensional scattergram of forward scattered light intensity (peak value) and fluorescence intensity. However, some types of *Bacillus* are large in size, and the intensity (peak) of forward scattered light detected with respect to such types of *Bacillus* becomes relatively high. For example, *Klebsiella pneumoniae* is large in size compared with bacteria of Enterobacteriaceae, such as *Escherichia coli*. When bacilli of such a type are contained by a large amount in a measurement sample, as shown in FIG. 19A, dot distribution similar to that in the case of coccus may occur.

FIG. 19A shows an example of a two-dimensional scattergram of forward scattered light intensity (peak value) and fluorescence intensity when a large number of large bacilli are contained in a measurement sample. FIG. 19B and FIG. 19C are the same two-dimensional scattergrams as in FIG. 7B and FIG. 7C, respectively.

With reference to FIG. 19A, even when the morphologic type of bacteria is *Bacillus*, dots are not distributed much in a lower region, and dot distribution in the scattergram in FIG. 19A becomes similar to dot distribution of the scattergrams of coccus shown in FIGS. 19B and 19C. Therefore, with respect to large bacilli, it is preferable to set a determination criterion that prevents occurrence of erroneous determination that the type of such large bacilli is coccus or a mixed-type.

Therefore, in a case where the morphologic type of bacteria is determined as coccus or the mixed-type by the above determination technique, it is preferable that the morphologic type of bacteria is re-determined in accordance with a criterion that is different from criteria of the above embodiment and the modifications, to correct the determination result.

FIG. 19D to FIG. 19F schematically show histograms showing the frequency of appearance of bacteria contained in lower regions A1 of FIG. 19A to FIG. 19C, respectively.

In a case where large bacilli are contained in the measurement sample, the intensity (peak) of forward scattered light becomes high. Thus, in the region A1 of FIG. 19A, in a range where forward scattered light intensity is high, the frequency of bacilli tends to be high. Therefore, the histogram corresponding to the bacteria in the region A1 of FIG. 19A tends to be the one shown in FIG. 19D, in general. The small peak in FIG. 19D corresponds to the frequency of contaminants other than bacteria.

In contrast, in each of the scattergram of *Streptococci* shown in FIG. 19B and the scattergram of *Staphylococci* shown in FIG. 19C, a large number of separate cocci are concentrated in a range where forward scattered light intensity is low, in general. Therefore, the histograms corresponding to the bacteria in the regions A1 of FIGS. 19B and 19C tend to be those shown in FIGS. 19E and 19F, in general. The peak in each of FIGS. 19E and 19F corresponds to the frequency of cocci when cocci have passed through the flow cell 203c without overlapping each other.

Therefore, the scattergram in FIG. 19A can be distinguished from the scattergrams in FIGS. 19B and 19C, by use of a parameter for the frequency of appearance of bacteria in a range where forward scattered light intensity is low. Therefore, by re-determining the morphologic type of bacteria by use of this parameter, whether the morphologic type of bacteria contained in the measurement sample is *Bacillus* (large *Bacillus*), or coccus or the mixed-type can be distinguished.

FIG. 20A to FIG. 20D each show an example of setting a parameter (hereinafter, referred to as "first re-determination parameter") for the frequency of appearance of bacteria in a region where forward scattered light intensity is low. In each of FIG. 20A to FIG. 20D, a histogram h3 indicating the frequency of appearance of bacteria contained in the region A1 when large bacilli are contained in the measurement sample, and a histogram h4 indicating the frequency of appearance of bacteria contained in the region A1 when cocci are mainly contained in the measurement sample are shown in an overlapping manner. It should be noted that, as shown in FIG. 19A to FIG. 19C, the region A1 includes a region near the origin of the scattergram.

For example, as the first re-determination parameter, a predetermined percentile value in a histogram of forward scattered light intensity can be used. Here, the percentile value is forward scattered light intensity when the frequency reaches a predetermined percent of the total frequency.

Figure 20A:
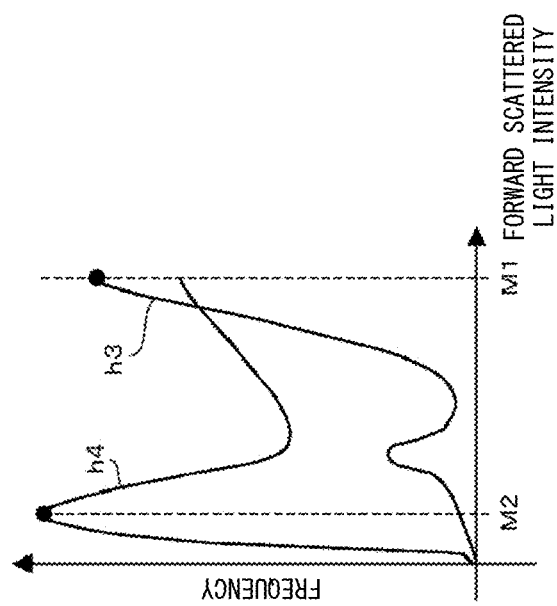
FIGS. 20A-20D show examples of setting parameters for the frequency of appearance of bacteria in a region where forward scattered light intensity is low according to the modification.

As shown in FIG. 20A, when large bacilli are contained in the measurement sample, the frequency of appearance of bacteria near the origin of the histogram is low, and when cocci are contained in the measurement sample, the frequency of appearance of bacteria near the origin of the histogram is very high. That is, a percentile value W1 in the histogram h3 where large bacilli are contained in the measurement sample is greater than a percentile value W2 in the histogram h4 where cocci are contained in the measurement sample. Therefore, in such a case, by comparing the percentile value as the first re-determination parameter with a predetermined threshold value, the case where large bacilli are contained in the measurement sample and the case where cocci are contained in the measurement sample can be distinguished from each other.

Further, as the first re-determination parameter, a peak value of the frequency of appearance in a histogram may be used.

Figure 20B:
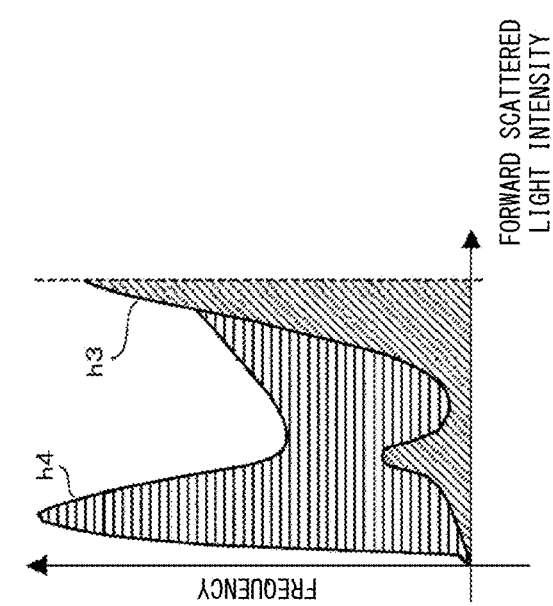

As shown in FIG. 20B, in the histogram h4, a frequency peak due to bacteria emerges near the origin. Thus, when the forward scattered light intensity is M2, the frequency of appearance of bacteria becomes the maximum. In contrast, in the histogram h3, no frequency peak due to bacteria emerges near the origin. Thus, when the forward scattered light intensity is M1, the frequency of appearance of bacteria becomes the maximum. Here, the forward scattered light intensity M1 is higher than the forward scattered light intensity M2. Therefore, by comparing, as the first re-determination parameter, the forward scattered light intensity at which the frequency of appearance becomes the maximum, with a predetermined threshold value, the case where large bacilli are contained in the measurement sample and the case where cocci are contained in the measurement sample can be distinguished from each other.

It should be noted that the maximum value of the frequency of appearance of bacteria in a range where forward scattered light intensity is lower than or equal to a predetermined percentile value may be used as the first re-determination parameter. Normally, this maximum value is greater in the histogram h4 than in the histogram h3. Therefore, by using this maximum value as the first re-determination parameter, whether the morphologic type of the bacteria contained in the measurement sample is *Bacillus* (large *Bacillus*), or coccus or the mixed-type can be distinguished.

Further, as the first re-determination parameter, a value of frequency of appearance of bacteria at a predetermined forward scattered light intensity may be used.

Figure 20C:
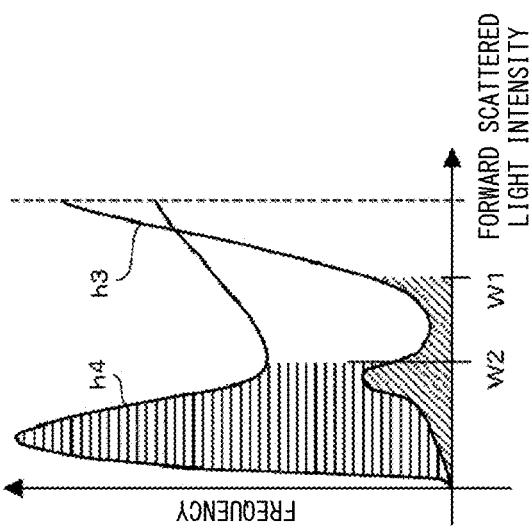

As shown in FIG. 20C, in the histogram h4, the frequency of appearance is sharply increased in a range where forward scattered light intensity is low, compared with that in the histogram h3. Therefore, when a predetermined forward scattered light intensity (FSC0) is set near the origin and the frequency of bacteria at this forward scattered light intensity (FSC0) is referred to, a frequency N1 in the histogram h3 is very low compared with a frequency N2 in the histogram h4. Therefore, by comparing, as the first re-determination parameter, the frequency of bacteria at the predetermined forward scattered light intensity (FSC0), with a predetermined threshold value, the case where large bacilli are contained in the measurement sample and the case where cocci are contained in the measurement sample can be distinguished from each other.

Further, as the first re-determination parameter, the total number of bacteria contained in a region where forward scattered light intensity is low may be used.

Figure 20D:
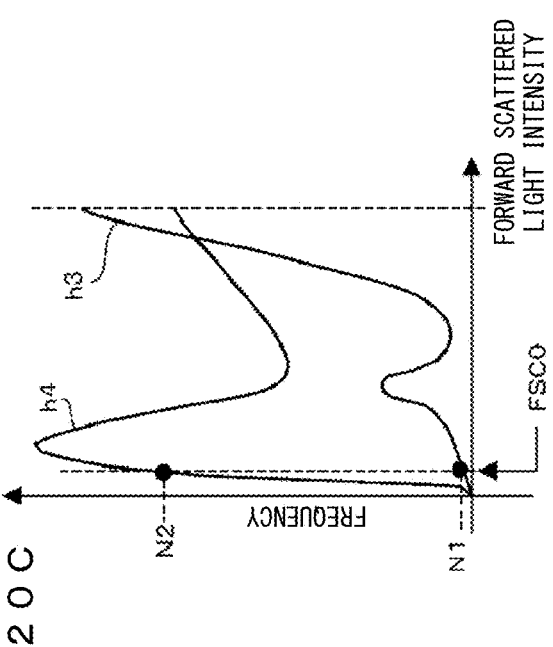

As shown in FIG. 20D, the area of the histogram h3 is smaller than the area of the histogram h4. Therefore, by comparing, as the first re-determination parameter, the total number of bacteria contained in the region where forward scattered light intensity is low, with a predetermined threshold value, the case where large bacilli are contained in the measurement sample and the case where cocci are contained in the measurement sample can be distinguished from each other. It should be noted that the region in which the total number of bacteria is obtained may be set to a region where forward scattered light intensity is further lower than that in the region A1 shown in FIGS. 19A to 19C.

Further, other than the first re-determination parameter described above, the parameter for re-determining the morphologic type of bacteria can be set as follows.

Figure 21A:
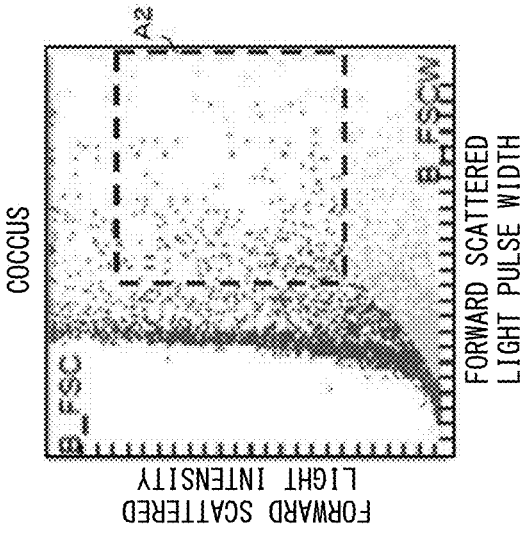
FIGS. 21A-21C illustrate scattergrams of forward scattered light intensity and forward scattered light pulse width in accordance with the morphologic type of bacteria according to a modification.
Figure 21B:
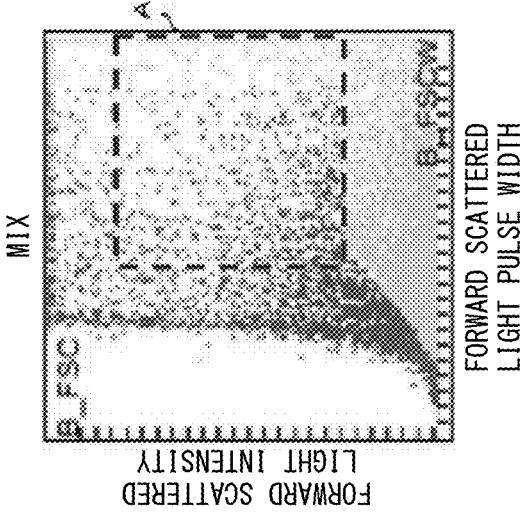
Figure 21C:
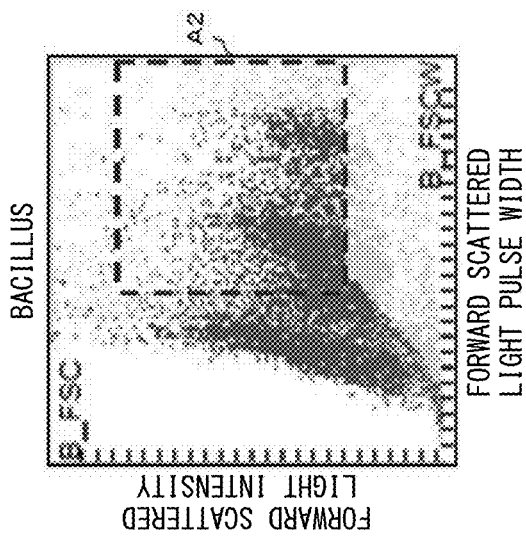

FIG. 21A illustrates a two-dimensional scattergram of forward scattered light intensity (peak value) and forward scattered light pulse width when a large number of large bacilli are contained in a measurement sample. FIG. 21B illustrates a two-dimensional scattergram of forward scattered light intensity (peak value) and forward scattered light pulse width when cocci and large bacilli are contained in a measurement sample. FIG. 21C illustrates a two-dimensional scattergram of forward scattered light intensity (peak value) and forward scattered light pulse width when cocci are contained in a measurement sample.

In measurement of bacteria, the longer the bacteria is, the longer the time period in which the bacteria is irradiated with laser light is, and thus, the forward scattered light pulse width, is increased accordingly.

When proliferating, cocci are likely to form an aggregate, and thus, even if they proliferate, the entire length thereof is less likely to increase. As shown in the lower part of FIG. 7A, in the case of *Bacillus*, each bacterium has an elongated rod or cylindrical shape, and thus, the more bacilli proliferate, the longer the entire length thereof is likely to become. Therefore, in a case where a large number of large bacilli are contained in a measurement sample, as shown in FIG. 21A, a two-dimensional scattergram in which dots are distributed in a wide range of forward scattered light pulse width is obtained. In contrast, as shown in FIG. 21B and FIG. 21C, in each case of the mixed-type (mix) and coccus, a two-dimensional scattergram is obtained in which dots are less distributed in a region where forward scattered light pulse width is large, compared with FIG. 21A.

Therefore, as shown in FIG. 19A, even when a large number of large bacilli are contained, by re-determining the morphologic type of bacteria by use of a parameter (hereinafter, referred to as "second re-determination parameter") for the frequency of appearance of bacteria in a region where forward scattered light pulse width is large in a two-dimensional scattergram of forward scattered light intensity (peak value) and forward scattered light pulse width, it is possible to accurately determine whether the morphologic type of bacteria contained in the measurement sample is *Bacillus* (large *Bacillus*) or coccus.

Of the region where forward scattered light pulse width is large, the region above a region A2 is highly likely to include a large number of aggregated cocci, and thus, is preferably excluded from the region to be used for re-determining the morphologic type of bacteria. Moreover, the region below the region A2 is highly likely to include contaminants, and thus, preferably is excluded from the region to be used for re-determining the morphologic type of bacteria. Therefore, in the present modification, as shown in FIG. 21A to FIG. 21C, by using a parameter for the frequency of appearance of bacteria in the region A2, which is the region where forward scattered light pulse width is large with the upper and lower regions excluded therefrom, the morphologic type of bacteria is re-determined.

As the second re-determination parameter, for example, the total number of bacteria contained in the region A2 can be used.

When FIG. 21A to FIG. 21C are compared with one another, in FIG. 21A, a large number of bacteria are contained in the region A2, and in FIGS. 21B and 21C, not so many bacteria are contained in the region A2. Therefore, by comparing, as a second re-determination parameter, the total number of bacteria contained in a region where forward scattered light pulse width is large, with a predetermined threshold value, the case where large bacilli are contained in the measurement sample and the case where cocci are contained in the measurement sample can be distinguished from each other.

Figure 22:
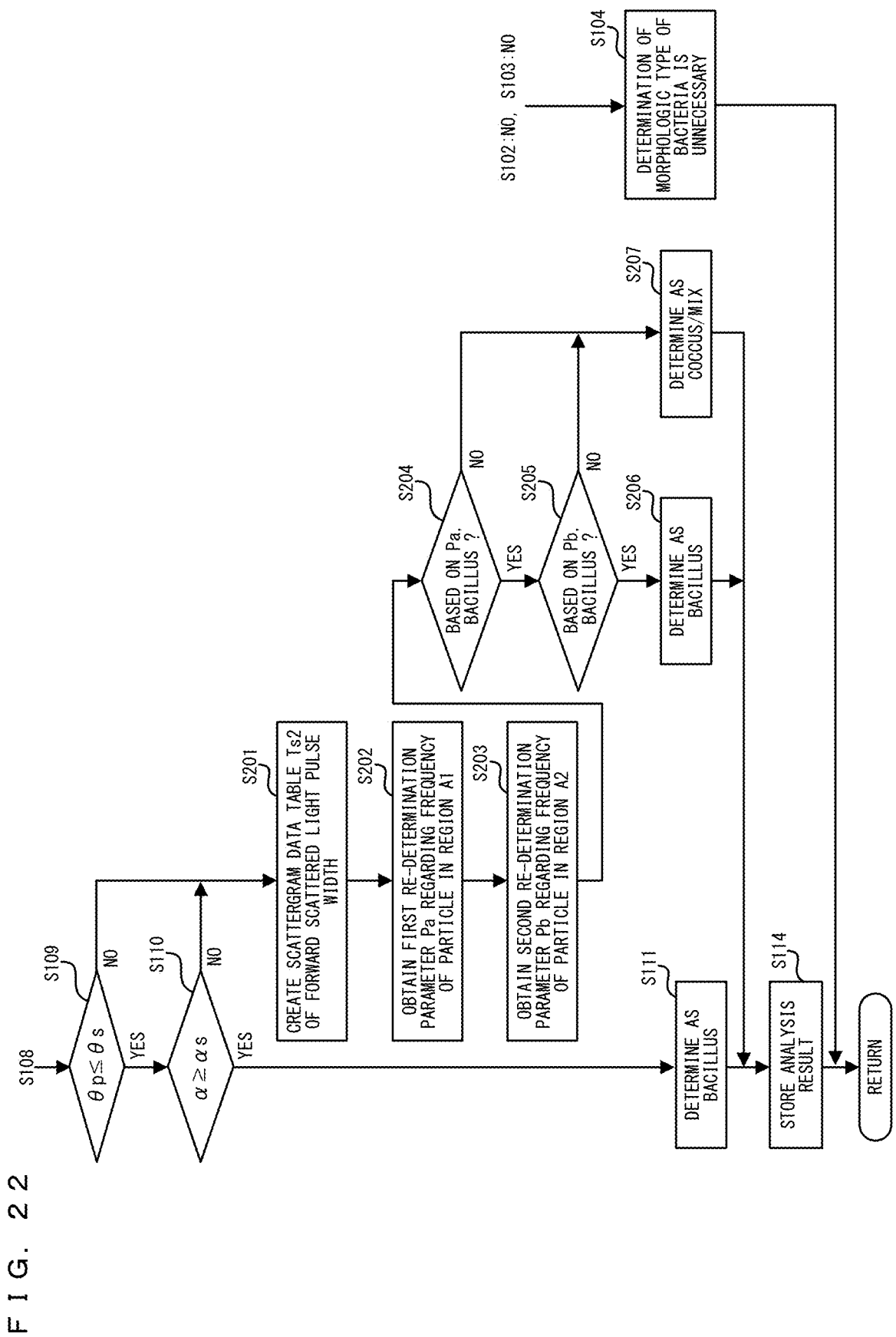
FIG. 22 is a flow chart showing an analysis process according to a modification.

FIG. 22 is a process flow chart of the analysis process according to the present modification. In the flow chart shown in FIG. 22, processes S201 to S207 are added. In the processes S201 to S207, when it has been determined that the morphologic type of bacteria is coccus or the mixed-type as a result of the determination as NO in S109 or S110 in FIG. 13, whether the morphologic type of bacteria is *Bacillus* or not is re-determined.

When the morphologic type of bacteria has been determined as coccus (S109: NO) or as the mixed-type (S110: NO) based on the declination information θp and the proportion α, the CPU 301 creates a scattergram data table Ts2 corresponding to the two-dimensional scattergram of forward scattered light intensity and forward scattered light pulse width shown in FIG. 21A (S201).

Next, based on the scattergram data table Ts created in S105 (see FIG. 13), the CPU 301 obtains a first re-determination parameter Pa for the frequency of particles in the region A1 (see FIG. 19A) in the two-dimensional scattergram of forward scattered light intensity and fluorescence intensity (S202). Moreover, based on the scattergram data table Ts2 created in S201, the CPU 301 obtains a second re-determination parameter Pb for the frequency of particles in the region A2 (see FIG. 21A) in the two-dimensional scattergram of forward scattered light intensity and forward scattered light pulse width (S203). When the first re-determination parameter Pa and the second re-determination parameter Pb have been obtained, the CPU 301 determines whether the first re-determination parameter Pa and the second re-determination parameter Pb respectively satisfy predetermined threshold value conditions indicating that bacteria are bacilli (S204, S205).

When the first re-determination parameter Pa satisfies the threshold value condition (S204: YES), and the second re-determination parameter Pb satisfies the threshold value condition (S205: YES), the CPU 301 determines, irrespective of the determination (S109: NO or S110: NO) based on the declination information θp and the proportion α, that the bacteria contained in the measurement sample are mainly bacilli (S206). On the other hand, when the first re-determination parameter Pa does not satisfy the threshold value condition (S204: NO) or when the second re-determination parameter Pb does not satisfy the threshold value condition (S205: NO), the CPU 301 determines, based on the determination (S109: NO or S110: NO) based on the declination information θp and the proportion α, that the morphologic type of bacteria is coccus or the mixed-type (mix) (S207).

FIG. 23A is a table showing results of determination of the morphologic type of bacteria according to the above embodiment performed on 85 urinary tract infection specimens. FIG. 23B is a table showing results of determination of the morphologic type of bacteria according to the present modification performed on 85 urinary tract infection specimens. In FIG. 23A, for comparison with the present modification, values each obtained by adding a value when the morphologic type has been determined as coccus and a value when the morphologic type has been determined as the mixed-type (mix) in the above embodiment are shown.

With reference to FIG. 23B, among 64 specimens determined as *Bacillus* in visual observation, 57 specimens were determined as *Bacillus* by the determination technique of the present modification. Moreover, among 21 specimens determined as coccus or the mixed-type (mix) in visual observation, 14 specimens were determined as coccus or the mixed-type (mix) by the determination technique of the present modification.

On the other hand, among 64 specimens determined as *Bacillus* in the determination results by the present modification, 57 specimens were determined as *Bacillus* also in visual observation. Moreover, among 21 specimens determined as coccus or the mixed-type (mix) in the determination results by the present modification, 14 specimens were determined as coccus or the mixed-type (mix) also in visual observation.

From the above, the concordance rate as a whole between the visual observation and the determination technique of the present modification was 83.5% (71/85), and it has been clarified that a higher determination accuracy than the concordance rate (77.6%) in the above embodiment shown in FIG. 23A was obtained. More specifically, the sensitivity to *Bacillus* was 89.1% (57/64), which means that *Bacillus* was determined more accurately than in the above embodiment (sensitivity: 78.1%). Other than this, the PPV for *Bacillus* was 89.1% (57/64), the sensitivity to coccus or the mixed-type (mix) was 66.7% (14/21), and the PPV for coccus or the mixed-type (mix) was 66.7% (14/21). Thus, the morphologic type of bacteria can be determined substantially as accurately as in the above embodiment.

As described above, with the configuration of the present modification, by re-determining the morphologic type of bacteria by use of the first re-determination parameter Pa and the second re-determination parameter Pb, the morphologic type of bacteria can be more accurately determined compared with the case where only the determination technique of the above embodiment is used.

In the above embodiment, the angle information (θk) corresponding to the angle region θk is the angle from the horizontal axis (fluorescence intensity) to the angle region θk. However, the angle from the vertical axis (forward scattered light intensity) to the angle region θk may be set as the angle information (θk) corresponding to the angle region θk.

In the above embodiment, the declination information θp is set to have the angle information of the angle region having the highest frequency of data (frequency of appearance of bacteria). However, the angle region based on which the declination information θp is obtained may not necessarily be the angle region having the highest frequency data, and may be set to an angle region near a region where the frequency of data becomes highest, such as an angle region adjacent to the angle region having the highest frequency of data.

In the above embodiment, as the proportion α, the proportion of the number of particles in a low angle region relative to the entirety of the particles is determined. However, the proportion of particles not in the low angle region but in an angle range included in a high angle side, relative to the entirety of the particles may be determined.

In the above embodiment, the declination information θp corresponding to the peak appearing in the histogram (FIG. 10A) created based on the declination calculated for each particle is used. However, the declination for each particle is not necessarily calculated. For example, the scattergram is divided into a plurality of regions defined by a predetermined angle about the origin, and the frequency of particles included in each region obtained by the division is counted, whereby the declination information θp may be determined.

Figure 24B:
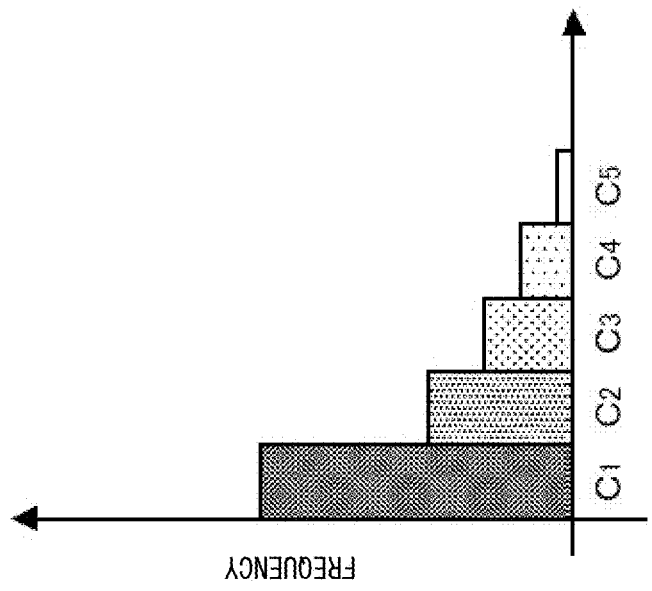
FIGS. 24A and 24B illustrate angle regions set on a scattergram of forward scattered light intensity and fluorescence intensity and a histogram according to a modification.
Figure 24A:
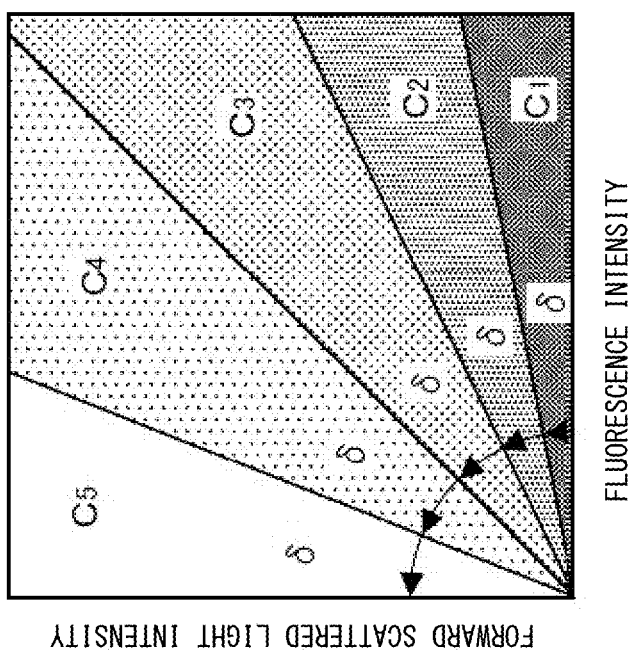

FIG. 24A illustrates the concept of angle regions C1 to C5 set on a two-dimensional scattergram according to the present modification. FIG. 24B illustrates a histogram showing the frequency of appearance of particles in each of the angle regions C1 to C5 according to the present modification. As in the two-dimensional scattergram shown in FIG. 8B, the two-dimensional scattergram in FIG. 24A has a horizontal axis representing fluorescence intensity and a vertical axis representing forward scattered light intensity.

In the present modification, first, as shown in FIG. 24A, the angle regions C1 to C5 defined by a predetermined angle δ are set on the two-dimensional scattergram. Then, by counting the total number of the frequencies of particles included in each of the angle regions C1 to C5, as shown in FIG. 24B, a histogram showing the frequency of each of the angle regions C1 to C5 is created. By determining the angle region in which the frequency peaks in this histogram, the declination information θp can be calculated.

As in the above embodiment, as shown in FIG. 9A, the region near the origin is preferably excluded from the target regions in which the number of particles are counted.

In the above embodiment, as the vertical axis of the feature space shown in FIG. 11A, FIG. 16A, FIG. 17A, and FIG. 18A, the declination information θp is used. However, instead, other information showing a characteristic of the distribution pattern of particles may be used. For example, without creating a histogram, by creating contour lines based on the frequency of particles shown in FIG. 25, information indicative of a characteristic of the distribution pattern of particles may be obtained.

Figure 25:
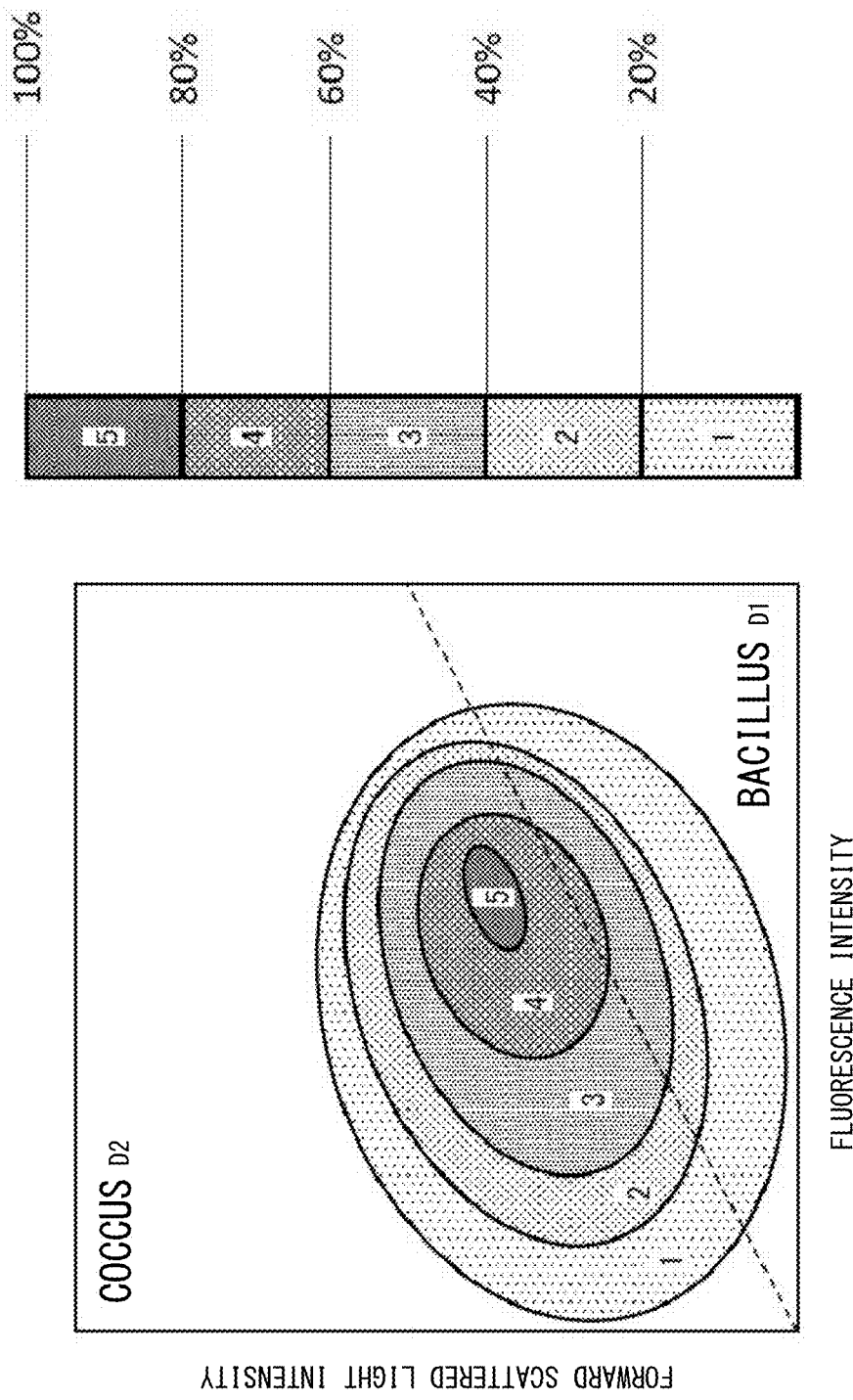
FIG. 25 illustrates contour line regions set on a scattergram of forward scattered light intensity and fluorescence intensity according to a modification.

FIG. 25 illustrates the concept of contour lines set on a two-dimensional scattergram according to the present modification. As in the two-dimensional scattergram shown in FIG. 8B, the two-dimensional scattergram shown in FIG. 25 has a horizontal axis representing fluorescence intensity and a vertical axis representing forward scattered light intensity.

First, the coordinate point at which the frequency of particles becomes maximum on the two-dimensional scattergram is determined. Next, in accordance with the frequency of each coordinate point, as shown in FIG. 25, a plurality of contour line regions are stepwise set on the two-dimensional scattergram. For example, the maximum value of frequency is defined as 100%, and contour line regions at five levels are set by 20%. The level 5 position corresponding to the vertex is used as information indicative of a characteristic of the distribution pattern of particles, instead of the declination information θp. Depending on whether the level 5 position is on the high angle side or on the low angle side relative to the broken line corresponding to a predetermined angle θs, the position in the vertical axis of the specimen in the feature space is determined. When the level 5 position is on the high angle side relative to θs, the specimen is plotted in the region S2. When the level 5 position is at θs or on the low angle side relative to θs, the specimen is plotted in the region S1 or S3.

In a case where the contour line region of level 5 extends across a low angle region D1 and a high angle region D2, then, in the contour line region of level 5, the total number of the frequencies of particles belonging to the low angle region D1 is compared with the total number of the frequencies of particles belonging to the high angle region D2, and then, it is determined that the contour line region of level 5 belongs to the region having the larger total number.

In the present modification, only the vertical axis in the feature space shown in FIG. 11A is determined. Therefore, as in the above embodiment, the proportion α of the number of particles included in the low angle region relative to the number of all particles is compared with a predetermined threshold value. Accordingly, whether particles are concentrated only in the low angle region is determined, and whether the morphologic type of bacteria is *Bacillus* or a mixed-type is determined.

Information indicative of a characteristic of the distribution pattern of particles may be the slope of a direction vector based on dispersion of particles on a two-dimensional scattergram.

Figure 26:
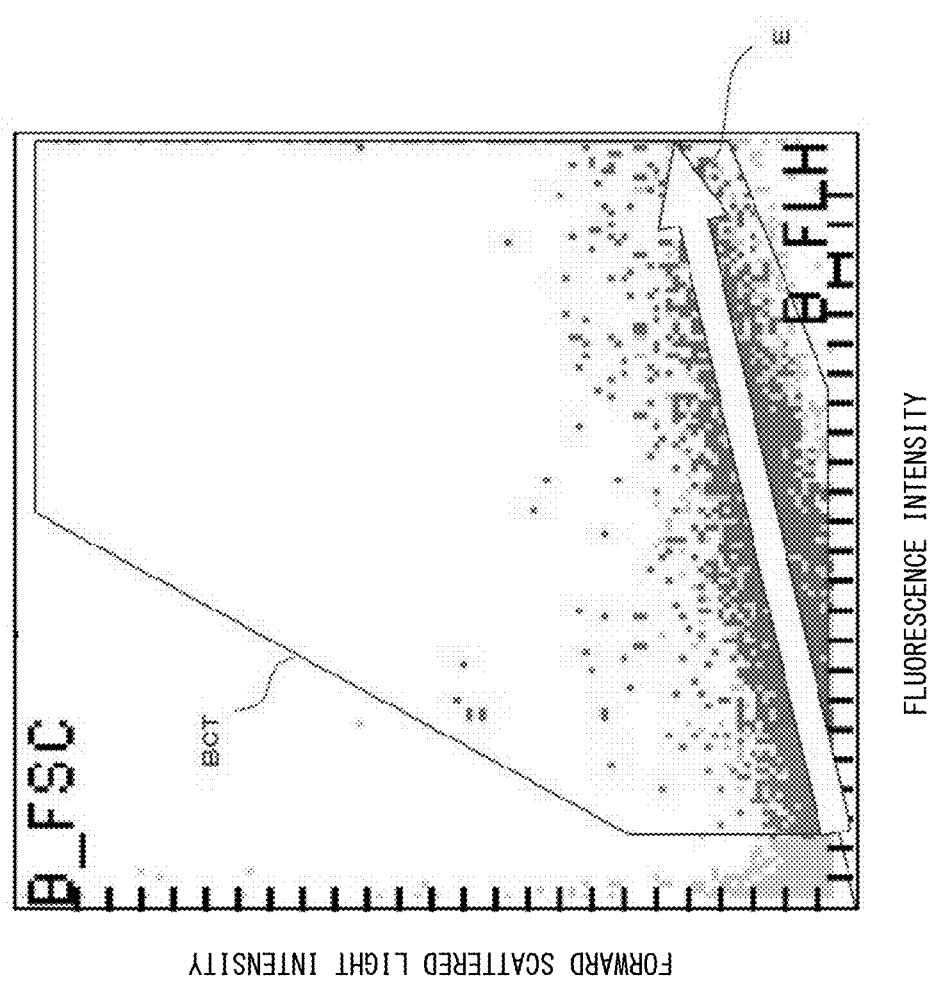
FIG. 26 illustrates a direction vector set on a scattergram of forward scattered light intensity and fluorescence intensity according to a modification.

FIG. 26 illustrates the concept of a direction vector E set on a two-dimensional scattergram. As in the two-dimensional scattergram shown in FIG. 8B, the two-dimensional scattergram in FIG. 26 has a horizontal axis representing fluorescence intensity and a vertical axis representing forward scattered light intensity.

In order to distinguish bacteria from other particles, a region BCT considered as a region where only bacteria appear is set. Only the particles having appeared within the region BCT are counted as bacteria. Dispersion of the particles present in the region BCT on a two-dimensional plane is determined. Then, the direction vector E which passes the center of dispersion and which indicates the maximum dispersion is determined. The slope of the direction vector E relative to the horizontal axis is used as information indicative of a characteristic of the distribution pattern of particles, instead of the declination information θp. Depending on whether the slope is greater than a predetermined angle θs, the position in the vertical axis of the specimen in the feature space is determined. When the slope is greater than θs, the specimen is plotted in the region S2. When the slope is equal to or smaller than θs, the specimen is plotted in the region S1 or S3.

The above-described determination technique of the morphologic type of bacteria using the slope of a direction vector based on dispersion of particles on a two-dimensional scattergram is described in Japanese Laid-Open Patent Publication No. 2004-305173 (corresponding U.S. Patent Application Publications No. US-2004-0219627-A1 and No. US-2014-0127794-A1) previously filed by the Applicant of this invention. The disclosure of Japanese Laid-Open Patent Publication No. 2004-305173 (corresponding U.S. Patent Application Publications No. US-2004-0219627-A1 and No. US-2014-0127794-A1) is incorporated herein by reference.

It is not necessary that the above-indicated exemplary information indicative of each of characteristics of the distribution pattern of particles is a representative value. For example, the entirety of the distribution pattern is compared with a distribution pattern of another specimen for which diagnosis was performed in the past, whereby the morphologic type of bacteria may be determined.

For example, as clinical data of patients for whom diagnosis was performed in the past, determination results obtained by a highly-reliable determination technique of the morphologic type of bacteria (for example, determination by visual observation) and distribution patterns of particles on two-dimensional scattergrams corresponding to these determination results are previously stored in the hard disk 304 (see FIG. 5) of the information processing apparatus 3 (see FIG. 5). When a two-dimensional scattergram is newly created, the distribution pattern of particles on this two-dimensional scattergram is compared with the past distribution patterns of particles on the two-dimensional scattergrams stored in the hard disk 304 (see FIG. 5), by use of a pattern matching technique. Through this comparison, a specimen having a distribution pattern most analogous to that of the newly created two-dimensional scattergram is extracted. The determination result of the morphologic type of bacteria of the extracted specimen is obtained as a provisional determination result.

Next, the proportion α of the number of particles included in a low angle region relative to the number of all particles is determined. Based on the proportion α, validity of the provisional determination result obtained by the pattern matching is evaluated. For example, as a result of the pattern matching, in a case where a specimen diagnosed as containing cocci only has been extracted as the most analogous specimen, there may be a case where the distribution pattern indicates a characteristic of coccus as a whole but when a partial region of the distribution pattern is focused, the partial region indicates a characteristic of *Bacillus*. In this case, it is preferable to provide the flag "mix", not the flag indicating coccus only. Accordingly, the laboratory technologist can confirm that a more detailed test such as determination by visual observation should be performed.

Moreover, in the form where classification into two morphologic types, i.e., "coccus or mixed-type" and "*Bacillus* only" is performed according to the embodiment and the modifications above, in both of a case where the morphologic type of bacteria is determined as "coccus or a mixed-type" and a case where the morphologic type of bacteria is determined as "*Bacillus* only", the declination information θp and the proportion α are used. However, when determining the morphologic type of bacteria as coccus or a mixed-type, the two parameters may not be necessarily used.

FIG. 27A shows the concept of a low angle region E1 and a high angle region E2 set on a two-dimensional scattergram according to the present modification. As in the two-dimensional scattergram shown in FIG. 8B, the two-dimensional scattergram shown in FIG. 27A has a horizontal axis representing fluorescence intensity and a vertical axis representing forward scattered light intensity.

With reference to FIG. 27A, the low angle region E1 and the high angle region E2 are set on the two-dimensional scattergram. As described above, when the morphologic type of bacteria is *Bacillus*, particles gather in the low angle region E1. If the frequency of particles included in the low angle region E1 is very small, the possibility that the morphologic type of bacteria is *Bacillus* is low, already at this time point. In this case, the number of bacteria is greater than or equal to a predetermined value (S103) and in addition, the possibility of *Bacillus* can be eliminated, and thus, it can be determined that the morphologic type of bacteria is coccus or a mixed-type.

FIG. 27B is a process flow chart of an analysis process according to the present modification. In the flow chart shown in FIG. 27B, processes of S301 to S305 are added, instead of S106 to S113 shown in FIG. 13.

With reference to FIG. 27B, in S105, when a scattergram data table Ts has been created, the CPU 301 calculates a total value Qa of frequencies of particles included in the low angle region E1 in the scattergram data table Ts (S301). The CPU 301 determines whether the total value Qa is smaller than a predetermined threshold value Qs (S302).

When the total value Qa obtained in S301 is smaller than the threshold value Qs (S302: YES), the CPU 301 determines that the morphologic type of bacteria is coccus or a mixed-type (mix) (S304). When the total value Qa is greater than or equal to the predetermined threshold value Qs (S302: NO), the CPU 301 determines whether the peak of the distribution of particles is in the high angle region E2 (S303). For this determination, the technique using the declination information θp or the technique described with reference to FIG. 24A and FIG. 24B is used. When the peak of the distribution of particles is in the high angle region E2 (S303: YES), the CPU 301 determines that the morphologic type of bacteria is coccus or a mixed-type (mix) (S304). For example, in a case where the total value Qa of frequencies of particles included in the low angle region E1 is large to some level but a large number of particles are also included in the high angle region E2, there is a high possibility that bacteria other than *Bacillus* are also included, and thus, it is determined that the morphologic type of bacteria is coccus or a mixed-type (mix). When the peak of the distribution of particles is not in the high angle region E2 (S303: NO), the CPU 301 determines that the morphologic type of bacteria is *Bacillus* (S305).

Then, as in the above embodiment, the CPU 301 stores the analysis result of the morphologic type of bacteria in the hard disk 304 (S114) and then ends the analysis process.

In the above embodiment, as shown in S102 and S103 in FIG. 13, the necessity/unnecessity of determination of the morphologic type of bacteria is determined by counting the number of bacteria and the number of white blood cells. However, the necessity/unnecessity may be determined only by counting the number of bacteria, or may be determined only by counting the number of white blood cells. Moreover, the determination processes of S102 and S103 may be omitted, or the necessity/unnecessity of performing these determination processes and threshold values therefor may be set by a user as appropriate.

In the above embodiment, the exemplary screen display in FIG. 14 is to be displayed, but the present invention is not limited thereto. For example, display of the two-dimensional scattergram and the histogram may be omitted as appropriate. Moreover, as reference information, the feature space, the distribution chart of measurement results, and the like shown in FIG. 16B may be displayed.

In addition to the above, various modifications of the embodiment of the present invention may be made as appropriate without departing from the scope of the technical idea defined by the claims.

What is claimed is:

1. A specimen analyzing method comprising:
   mixing, in a mixing chamber, a urine specimen and a reagent to prepare a measurement sample in which a bacterium is stained with fluorescent dye;
   flowing the measurement sample in a flow cell;
   irradiating light onto the measurement sample running in the flow cell;
   detecting scattered light and fluorescence, produced in response to an irradiation, of individual bacteria in the measurement sample and generating digital data of individual bacteria according to intensities of detected scattered light and fluorescence;
   digitally plotting the digital data of the individual bacteria according to the intensities of the detected scattered light and fluorescence on a coordinate space having a first axis of scattered light intensity and a second axis of fluorescent intensity to analyze a distribution of plots of the individual bacteria on the coordinate space, thereby acquiring:
   (i) a declination representative of a peak angle region having a largest number of plots among a plurality of angle regions in a first region of the coordinate space, wherein the angle regions define a plurality of spaces radially divided by a constant angle about the origin in the first region, wherein the peak angle region is the angle region where a peak appears in a frequency distribution of plots in each of the angle regions, and wherein the declination is the angle between a radial line originating at the origin that defines an edge of the peak angle region and an axis of the coordinate space, and
   (ii) a proportion of a number of plots in a second region relative to a number of plots in the first region, wherein the second region is a part of the first region and wherein the second region is represented as an angle region about the origin defined by a first line originating at the origin at a preset angle relative to the second axis and a second line originating at the origin that also bounds an edge of the first region, and
   determining, based on (i) the declination of the peak angle region and (ii) the proportion, whether the specimen contains Bacillus, coccus, or both.

2. The specimen analyzing method of claim 1, wherein the first region is an angle region defined at an upper edge by a third line originating at the origin at a second angle relative to the second axis, wherein the second angle is greater than the preset angle.

3. The specimen analyzing method of claim 1, wherein the specimen is determined as containing Bacillus when both of following conditions are met:
   the information (i) is lower than a first threshold value, and
   the information (ii) is greater than or equal to a second threshold.

4. The specimen analyzing method of claim 1, wherein the specimen is determined as containing coccus, or a mix of Bacillus and coccus, when at least one of following conditions are met:
   the information (i) is greater than a first threshold value, or the information (ii) is smaller than a second threshold value.

5. The specimen analyzing method of claim 1, wherein the specimen is determined as containing a mix of Bacillus and coccus when both of following conditions are met:
   the information (i) is lower than a first threshold value, and
   the information (ii) is smaller than a second threshold value.

6. The specimen analyzing method of claim 1, wherein the specimen is determined as containing coccus when the information (i) is greater than a first threshold value.

7. The specimen analyzing method of claim 1, wherein the specimen is determined as containing Bacillus, coccus, or both also based on:
   (iii) a determination of a higher number of bacteria plots toward a high value side relative to a low value side of a light intensity threshold indicating a size of bacteria.

8. The specimen analyzing method of claim 7, wherein the specimen is determined as containing Bacillus, when the information (i) and the information (ii) correspond to a characteristic of coccus or a mix of Bacillus and coccus, but the information (iii) indicates a higher number of plots corresponding to Bacillus.

9. The specimen analyzing method of claim 1, wherein the specimen is determined as containing Bacillus, coccus, or both also based on:
   (iv) a determination of optical characteristics of bacteria that varies in accordance with a length of a single Bacillus bacterium or a number of chains of streptococcus bacteria contained in a single aggregate.

10. The specimen analyzing method of claim 9, wherein the specimen is determined as containing Bacillus when the information (i) and the information (ii) correspond to a characteristic of coccus or a mix of Bacillus and coccus, but the information (iv) indicates a characteristic corresponding to Bacillus.

11. The specimen analyzing method of claim 1, further comprising:
    displaying the determination of whether the specimen contains Bacillus, coccus, or both.

12. The specimen analyzing method of claim 1, further comprising:
    obtaining a number of bacteria and a number of white blood cells contained in the specimen, wherein
    the determination of whether the specimen contains Bacillus, coccus, or both, is displayed when the number of bacteria is greater than a third threshold value and the number of white blood cells is greater than a fourth threshold value.

13. The specimen analyzing method of claim 11, further comprising:
    displaying a scattergram showing a distribution pattern of the plots contained in the measurement sample along the two respective axis.

14. The specimen analyzing method of claim 13, wherein the scattergram and the determination of whether the specimen contains Bacillus, coccus, or both, are displayed on a same screen.

* * * * *